US005763631A

United States Patent [19]
Kim et al.

[11] Patent Number: 5,763,631
[45] Date of Patent: Jun. 9, 1998

[54] IRREVERSIBLE HIV PROTEASE INHIBITORS, INTERMEDIATES, COMPOSITIONS AND PROCESSES FOR THE PREPARATION THEREOF

[75] Inventors: Sung Chun Kim; Nakyen Choy; Chang Sun Lee; Ho L Choi; Jong Sung Koh; Heungsik Yoon; Chi Hyo Park; Sang Soo Kim; Young Chan Son, all of Daejeon, Rep. of Korea

[73] Assignee: Lucky Limited, Seoul, Rep. of Korea

[21] Appl. No.: 667,133

[22] Filed: Jun. 20, 1996

Related U.S. Application Data

[62] Division of Ser. No. 159,382, Nov. 30, 1993, Pat. No. 5,587,388.

[30] Foreign Application Priority Data

| Dec. 2, 1992 | [KR] | Rep. of Korea | 92-23088 |
| Dec. 2, 1992 | [KR] | Rep. of Korea | 92-23089 |
| Jun. 14, 1993 | [KR] | Rep. of Korea | 93-10811 |
| Oct. 14, 1993 | [KR] | Rep. of Korea | 93-21298 |
| Oct. 14, 1993 | [KR] | Rep. of Korea | 93-21299 |
| Oct. 14, 1993 | [KR] | Rep. of Korea | 93-21300 |

[51] Int. Cl.[6] ............ C07D 303/08; C07D 215/38; C07D 235/04; C07D 413/00
[52] U.S. Cl. ............ 549/552; 546/169; 546/268; 548/304.7; 544/147
[58] Field of Search ............ 549/552; 546/169, 546/268; 548/304.7; 544/147

[56] References Cited

U.S. PATENT DOCUMENTS 5,545,750  8/1996  Kempf et al. ............ 564/360
5,587,385  12/1996  Kim et al. ............ 514/314

*Primary Examiner*—Deborah Lambkin
*Attorney, Agent, or Firm*—Anderson, Kill & Olick, P.C.

[57] ABSTRACT

Cis-epoxide compounds of formula (I-3) and pharmaceutically acceptable salts, hydrates and solvates thereof:

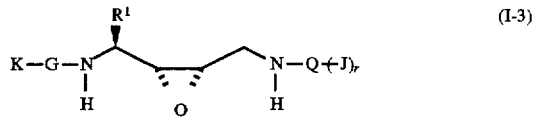

(I-3)

wherein:
$R^1$ is a cycloalkyl, or arly-substituted lower alkyl group;
K and J are independently a group having the formula of

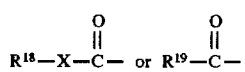

wherein $R^{18}$ is a lower alkyl group optionally substituted with an aryl radical; X is O, NH, or N—CH$_3$; and $R^{19}$ is an aromatic hetercyclic sysstem containing a nitrogen atom in its ring, or a lower alkyl group optionally substituted with an aryl radical, or a hydrogen;

G is an amino acid which is linked to K— and

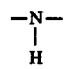

by peptide bonds in formula (I-3);
Q is an amino acid which is linked to
by peptide bonds in formula (I-3), or a group having the formula of
wherein $R^{20}$ is a lower alkyl group optionally substituted with an aromatic radical; and Y is CH$_2$, O or NH; and
r is 0 or 1, except that Q is a group having the formula of r is 0.

1 Claim, 1 Drawing Sheet

IRREVERSIBLE HIV PROTEASE INHIBITORS, INTERMEDIATES, COMPOSITIONS AND PROCESSES FOR THE PREPARATION THEREOF

This is a division of application Ser. No. 08/159,382, filed Nov. 30, 1993, now U.S. Pat. No. 5,587,388.

FIELD OF THE INVENTION

The present invention relates to novel compounds for inhibiting human immunodeficiency virus ("HIV") protease, their intermediates, pharmaceutical compositions containing the compounds as active ingredients, and processes for the preparation of the compounds and the intermediates.

BACKGROUND OF THE INVENTION

HIV which is known to cause AIDS(acquired immunodeficiency syndrome) is one of retroviruses which contain their genetic information in RNA; and consists of a core, envelope proteins, a lipid membrane and glycoproteins. The HIV core comprising two single-stranded RNA and reverse transcriptase is enclosed by envelope proteins such as p17, p9, p24, p7 and the like, which are in turn enclosed by a lipid membrane.

Glycoproteins located outside of the lipid membrane consist of gp41 and gp120, of which gp120 plays a major role to recognize and infect T cells.

Similar to other retroviruses, HIV is unusual in that its growth cycle has a stage in which the flow of information is reversed(that is, RNA→DNA) contrary to the usual mechanism (DNA→RNA).

For such a reverse mechanism, the existence of a reverse transcriptase which makes double-stranded DNA from a single-stranded RNA template is essential; and, consequently, only retroviruses have a reverse transcriptase.

Accordingly, it has been predicted that HIV can be incapacitated by way of inhibiting the activity of the reverse transcriptase; and, hitherto, many reverse transcriptase inhibitors have been developed. Such inhibitors include: 3-azido-3'-deoxythymidine(AZT) developed by Burrows-Wellcome Co.; 2',3'-dideoxyinosine(DDI) of Bristol Meyers Squibb Co; and 2',3'-dideoxycytosine(DDC) of F. Hoffmann-La Roche AG.

However, the above and other compounds known in the art as a treating agent for AIDS have shown rather limited effect of prolonging patients' life; and, further, tend to cause serious side effects such as decrease of the number of blood platelets, kidney infection, bone marrow toxicity, and the like.

Another important enzyme active during HIV replication is HIV protease responsible for the proteolytic processing of polyprotein precursors. Gag protein(p55) and gal-pol protein (p165) are processed into structural envelope proteins and essential functional proteins for HIV replication such as protease, reverse transcriptase, integrase, etc. (see Henderson et al., J. Virol. 62, 2587(1988)). Accordingly, HIV protease inhibitors have been also considered as a potential AIDS treating agent.

HIV protease is present in a dimeric form having a $C_2$ symmetry; and, each monomer has a molecular weight of 10,793 daltons and consists of 99 amino acids. HIV protease is classified as an aspartic protease since it is proved to have the typical sequence of Asp-Thr-Gly at the active site, and can be inhibited by pepstatin, a known inhibitor of aspartic proteases. Pepstatin has a hydroxyethyl group instead of a peptide bond at the site where reaction with a protease occurs, which is similar to the form of a transition state during the protease reaction; and, it appears that the form having a hydroxyethyl group binds to a protease more strongly than a polypeptide having a peptide bond; and, therefore, pepstatin prohibits a protease reaction.

In this connection, recent studies on HIV protease inhibitors have been focused on the development of compounds similar to the transition state which has a high affinity to the protease(see Roberts et al., Science 248, 358(1990); Signal et al., EP Publication No. 0337714; Handa et al., EP Publication No. 0346847; Desolms et al., EP Publication No. 0356223; Dreyer et al., EP Publication No. 0352000; Signal et al., EP Publication No. 0357332; Hanko et al., EP Publication No 0361341; Kempf et al., Korean Patent Laid-open Publication No. 90-18134; Bone et al., J. Am. Chem. Soc. 113, 9382(1991); and Urban et al., FEBS Letter 298, 9(1992)).

These compounds, however, suffer from the deficiency that they are reversible inhibitors. The irreversible inhibitors would be more desirable because they could block the protease activity permanently. Accordingly, efforts have been made for the development of irreversible inhibitors by way of introducing an epoxide to the reaction site thereof (see Moelling et al., FEBS Letter 261, 373(1990); Pal et al., Proc. Natl. Aca. Sci. 85, 9283(1988); Grant et al., Bioorg. Med. Chem. Letter 2, 1441(1992); and EP Publication No. 0492136A). However, these irreversible inhibitors have too limited inhibitory effect to be useful as an AIDS treating agent.

SUMMARY OF THE INVENTION

Accordingly, it is a primary object of the present invention to provide irreversible HIV protease inhibitors having a high inhibitory effect against HIV protease, useful for the treatment of AIDS.

Another object of the present invention is to provide novel compounds useful as intermediates for preparing the inhibitors.

A further object of she present invention is to provide processes for preparing said inhibitors and intermediates.

A still further object of the present invention is to provide pharmaceutical compositions containing the inhibitors in a therapeutically effective amount as active ingredients, and pharmaceutically acceptable carriers.

In accordance with one aspect of the present invention, there are provided novel HIV protease inhibitors prepared to have a cis-epoxide capable of reacting with an aspartyl group, based on the observation that HIV protease is an aspartic protease.

DETAILED DESCRIPTION OF THE INVENTION

Figure 1:
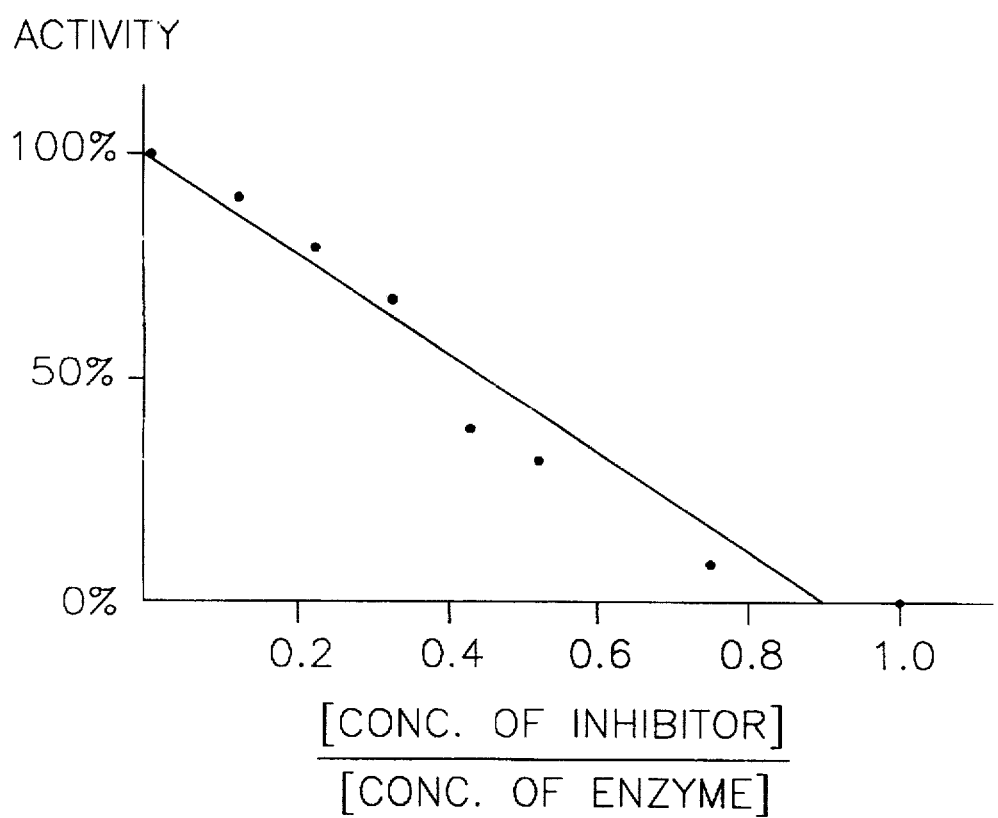
FIG. 1 is a graph representing the stoichiometric ratios of the novel inhibitors over the enzyme for the inactivation.

In accordance with the present invention, there are provided novel cis-epoxide compounds of formula (I-1) and pharmaceutically acceptable salts, hydrates and solvates thereof:

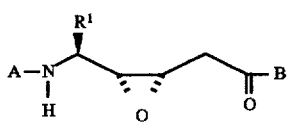
(I-1)

wherein:

$R^1$ is a cycloalkyl, or aryl-substituted lower alkyl group;
A is a functionalized acyl group of the formula

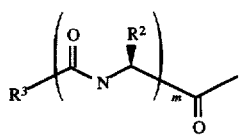

(wherein $R^2$ is a $C_{1-4}$ alkyl, or amide-substituted $C_{1-2}$ alkyl group; $R^3$ is a $C_{1-4}$ alkoxy, aryloxyalkyl or arylalkoxy, or a nitrogen-containing aromatic radical, or a lower alkoxy group substituted with a nitrogen-containing aromatic radical, or a radical having the formula of

(wherein $R^4$ is a hydrogen or a methyl group and $R^5$ is an alkyl group substituted with a nitrogen-containing aromatic radical); and m is 0 or 1); and B is a functionalized amino group of the formula

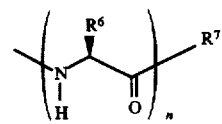

(wherein $R^6$ is a $C_{1-4}$ alkyl, arylalkyl, or amide-substituted $C_{1-2}$ alkyl group; $R^7$ is a $C_{1-3}$ alkoxy, $C_{1-3}$ alkylamino, $C_{1-3}$ alkoxyamino or amino group substituted with two $C_{1-3}$ alkyl groups, or an oxygen-containing heterocyclic amino group or a lower alkyl amino group substituted with a nitrogen-containing aromatic heterocyclic system; and n is 1 or 2), a functionalized amino group of the formula

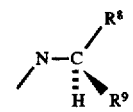

(wherein $R^8$ and $R^9$ are independently a $C_{1-4}$ alkyl group optionally substituted with an aromatic radical, or an aromatic group), or a hydroxy-substituted cycloalkylamino system fused with an aromatic ring.

Among the compounds of formula (I-1), preferred are those wherein:

$R^1$ is a cyclohexylmethyl or benzyl group; A is a group having the formula of

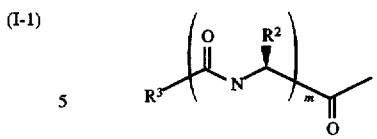

wherein $R^3$ is a phenoxymethylcarbonyl, naphthoxymethylcarbonyl, quinalinylcarbonyl, pyrimidinylcarbonyl, benzimidazolylcarbonyl or benzyloxycarbonyl group, and $R^2$ is an asparagine or valine residue; and B is (2R)-hydroxy-(1S)-indanylamino group, or a group having the formula of

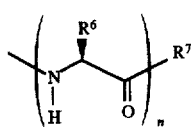

wherein $R^6$ is an isoleucine, phenylalanine, glutamine or valine residue, or a combination thereof consisting of two amino acids, and $R^7$ is a methoxy, ethoxy, methylamino, dimethylamino, ethylamino, t-butylamino, benzylamino, benzimidazol-2-yl-methylene amino or pyridine-2-yl-methyleneamino group, or a group having the formula of

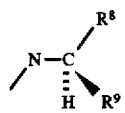

wherein $R^8$ and $R^9$ are independently an isopropyl, phenyl, benzyl, phenylethyl or phenylpropyl group; and pharmaceutically acceptable salts, hydrates and solvates thereof.

In accordance with the present invention, there are further provided novel cis-epoxide compounds of formula (I-2) and pharmaceutically acceptable salts, hydrates and solvates thereof:

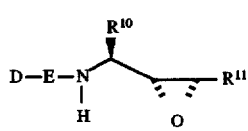
(I-2)

wherein:

$R^{10}$ and $R^{11}$ are independently a lower alkyl or arylalkyl group;
D is

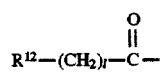

(wherein $R^{12}$ is an aryl, lower alkyl, aryloxy group optionally substituted with a halogen or a hydroxy radical, a nitrogen-containing aromatic heterocyclic system or N-oxide system thereof, or a 3- to 6-membered heterocyclic system containing a nitrogen atom alone or together with an oxygen atom as heteroatom(s); and l is 0, 1 or 2),

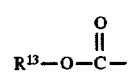

(wherein $R^{13}$ is a lower alkyl or arylalkyl group), or

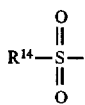

(wherein $R^{14}$ is an aliphatic heterocyclic system containing oxygen and nitrogen atoms); and E is of the formula

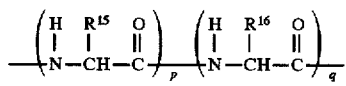

(wherein $R^{15}$ is a lower alkyl or aryl alkyl group; $R^{16}$ is a lower alkyl group optionally substituted with an amide; and p and q are independently 0 or 1).

Among the compounds of formula (I-2), preferred are those wherein:

$R^{10}$ is a benzyl, cyclohexylmethyl or isobutyl group;

$R^{11}$ is a phenylethyl or isopentyl group;

D is a phenoxymethylcarbonyl, naphthoxymethylcarbonyl, quinalinylcarbonyl, or benzyloxycarbonyl group; and E is an amino acid such as asparagine, valine, isoleucine, phenylalanine, alanine or glutamine, or a combination thereof consisting of two amino acids.

In accordance with the present invention, there are still further provided novel cis-epoxide compounds of formula (I-3) and pharmaceutically acceptable salts, hydrates and solvates thereof:

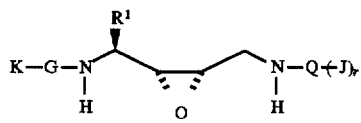 (I-3)

wherein:

$R^1$ has the same meaning as defined previously;

K and J are independently a group having the formula of

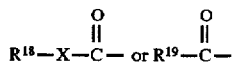

(wherein $R^{18}$ is a lower alkyl group optionally substituted with an aryl radical; X is O, NH, or N—$CH_3$; and $R^{19}$ is an aromatic heterocyclic system containing a nitrogen atom in its ring, or a lower alkyl group optionally substituted with an aryl radical, or a hydrogen);

G is an amino acid which is linked to K— and

by peptide bonds in the formula (I-3);

Q is an amino acid which is linked to

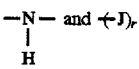

by peptide bonds in the formula (I-3), or a group having the formula of

(wherein $R^{20}$ is a lower alkyl group optionally substituted with an aromatic radical; and Y is $CH_2$, O or NH); and r is 0 or 1; except that when Q is a group having the formula of

r is 0.

Among the compounds of formula (I-3), preferred are those wherein:

$R^1$ is a cyclohexylmethyl or benzyl group;

K is a benzyloxycarbonyl, naphthoxymethylcarbonyl, pyridylmethylaminocarbonyl, N-pyridylmethyl-N-methylaminocarbonyl, quinolinylcarbonyl, benzimidazolylcarbonyl or pyridylmethyloxycarbonyl group;

G is a leucine, valine, isoleucine, phenylalanine, phenylglycine, serine, glutamic acid, asparagine, or glutamine;

J is the formula of

wherein $R^{19}$ is a hydrogen, benzyloxy, naphtoxymethyl, quinalinyl, pyridylmethylamino, N-pyridylmethyl-N-methylamino, benzimidazolyl, or pyridylmethyloxy; and Q is a leucine, valine, isoleucine, phenylalanine, phenylglycine, serine, glutamic acid, asparagine, or glutamine; and in case r=0, Q is t-butoxycarbonyl.

As used hereinabove, and else where in this specification the following terms shall have the following meanings:

The term "lower alkyl" refers to a $C_{1-6}$ straight or branched alkyl including methyl, ethyl, isopropyl, isobutyl and t-butyl, preferably, methyl.

The term "lower alkyl or alkoxy substituted with an aromatic radical" means lower alkyl or alkoxy, preferably $C_{1-2}$ alkyl or alkoxy, substituted with an aromatic radical in the position of the end carbon of straight chain, preferably, benzyl.

The term "nitrogen-containing aromatic heterocyclic system" refers to monocyclic or bicyclic aromatic radical containing 1 to 3 nitrogen atoms in the ring, for example, including pyridine, quinoline, quinoxaline and benzimidazole, and preferably, quinoline; and "N-oxide system thereof" refers to the above aromatic radical wherein the nitrogen atom(s) is linked to oxygen atom.

The term "aryl" means monovalent monocyclic or bicyclic aromatic radical, for example, phenyl and naphthalene.

The term "3- to 6-membered heterocyclic system containing nitrogen atom alone or together with oxygen atom" refers to heterocyclic aliphatic or aromatic system containing at least 1(one) nitrogen atom alone or together with oxygen atom in the ring, for example, imidazole, triazole and morpholine.

The term "aryl-substituted lower alkyl" refers to lower alkyl substituted with aryl or arylalkoxy including phenoxy and naphthoxy, preferably, benzyl.

The term "amino acid" means preferably asparagine, valine, threonine, isoleucine and glutamic acid.

In this specification, standard three letter abbreviations are used to represent amino acids. The meanings of these abbreviations can be found in, for example, Eur. J. Biochem. 158, 9–31(1984).

The compounds of the present invention may have one or more asymmetric carbon; and, therefore, the present invention encompasses, within its scope, racemic mixtures, mixtures of diastereomers, as well as single diastereomers of the compounds of the invention and pharmaceutically acceptable salts, hydrates and solvates thereof.

Important compounds of the present invention are listed in Tables 1 to 3 below.

TABLE 1

(I-1)

| Comp. No. | A | R¹ | B |
|---|---|---|---|
| 1 | [Cbz-Asn] | [benzyl] | [NH-CH(sec-Bu)-COOCH₃, N-methyl] |
| 2 | [quinoline-2-carbonyl-Asn] | " | " |
| 3 | [1-naphthyloxyacetyl-Asn] | " | " |
| 4 | [phenoxyacetyl-Asn] | " | " |
| 5 | [quinoline-2-carbonyl-Asn] | [cyclohexylmethyl] | " |
| 6 | " | [benzyl] | [N-methyl-Ile-Val-COCH₃] |

TABLE 1-continued
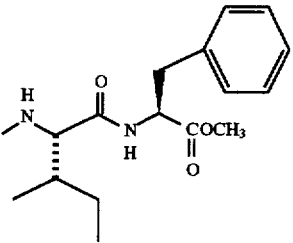
| Comp. No. | A | R¹ | B |
|---|---|---|---|
| 7 | " | " | 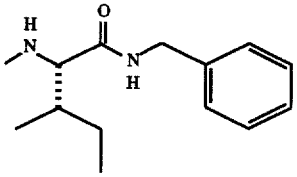 |
| 8 | " | " | 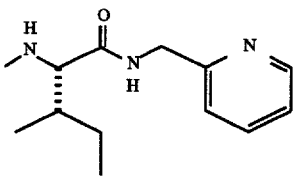 |
| 9 | " | " | 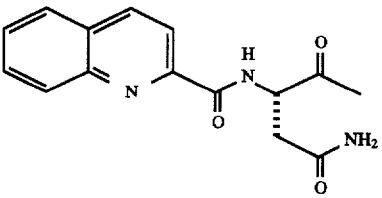 |
| 10 | 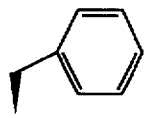 | 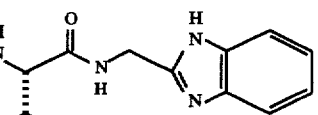 | 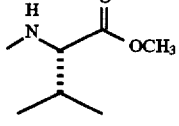 |
| 11 | " | " | 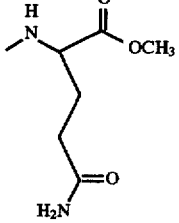 |
| 12 | " | " |  |

TABLE 1-continued $$\text{A}-\underset{\text{H}}{\text{N}}-\overset{R^1}{\underset{\text{O}}{\text{C}}}-\overset{\text{B}}{\underset{\text{O}}{\text{C}}}\quad (I\text{-}1)$$

| Comp. No. | A | R¹ | B |
|---|---|---|---|
| 13 | (benzyloxycarbonyl-Asn) | " | (N-methyl-Gln-OCH₃) |
| 14 | (quinoline-2-carbonyl-Asn) | " | (N-methyl-Gln-Phe-OCH₃) |
| 15 | " | " | (N-methyl-2-hydroxyindan-1-yl) |
| 16 | (1-naphthyloxyacetyl-Asn) | " | (N-methyl-Gln-Val-OCH₃) |
| 17 | (quinoline-2-carbonyl-Asn) | " | (N-methyl-Val-Val-OCH₃) |
| 18 | " | " | (N-methyl-Val-Phe-OCH₃) |

TABLE 1-continued $$\text{A-N}^{H}\text{-}\overset{R^1}{\underset{O}{C}}\text{-}\overset{}{\underset{O}{C}}\text{-B} \quad (I-1)$$

| Comp. No. | A | R¹ | B |
|---|---|---|---|
| 19 | quinoline-2-carbonyl-NH-CH(CH₂C(O)NH₂)-C(O)- | benzyl | -NH-CH(iPr)-C(O)-NH-CH₂-(2-pyridyl) |
| 20 | " | " | -NH-CH(iPr)-C(O)-NH-CH₂-(1H-benzimidazol-2-yl) |
| 21 | quinoline-2-carbonyl-NH-CH(iPr)-C(O)- | " | -NH-CH(sec-Bu)-C(O)-OCH₃ |
| 22 | " | " | -NH-CH(iPr)-C(O)-NH-CH₂-(2-pyridyl) |
| 23 | " | " | -NH-CH(iPr)-C(O)-NH-CH₂-(1H-benzimidazol-2-yl) |
| 24 | " | " | -NH-CH(iPr)-C(O)-NH-CH(CH₂Ph)-C(O)-OCH₃ |
| 25 | quinoline-2-carbonyl-NH-CH(CH₂C(O)NH₂)-C(O)- | benzyl | -NH-CH(sec-Bu)-C(O)-NH-CH₃ |

TABLE 1-continued (I-1) Structure: A-NH-CH(R¹)-[epoxide]-CH₂-C(O)-B

| Comp. No. | A | R¹ | B |
|---|---|---|---|
| 26 | quinoline-2-carbonyl-NH-CH(CH₂C(O)NH₂)-C(O)- | benzyl | -NH-CH(CH(CH₃)CH₂CH₃)-C(O)-N(CH₃)₂ |
| 27 | quinoline-2-carbonyl-NH-CH(CH₂C(O)NH₂)-C(O)- | benzyl | -NH-CH(CH(CH₃)CH₂CH₃)-C(O)-NH₂ |
| 28 | quinoline-2-carbonyl-NH-CH(CH₂C(O)NH₂)-C(O)- | benzyl | -NH-CH(CH(CH₃)CH₂CH₃)-C(O)-NH-OCH₃ |
| 29 | quinoline-2-carbonyl-NH-CH(CH₂C(O)NH₂)-C(O)- | benzyl | -NH-CH(CH(CH₃)CH₂CH₃)-C(O)-morpholinyl |
| 30 | quinoline-2-carbonyl-NH-CH(CH₂C(O)NH₂)-C(O)- | benzyl | -NH-CH(CH(CH₃)₂)-C(O)-NH-CH₃ |
| 31 | quinoline-2-carbonyl-NH-CH(CH₂C(O)NH₂)-C(O)- | benzyl | -NH-CH(CH(CH₃)₂)-C(O)-N(CH₃)₂ |
| 32 | quinoline-2-carbonyl-NH-CH(CH₂C(O)NH₂)-C(O)- | benzyl | -NH-CH(CH(CH₃)₂)-C(O)-NH₂ |

TABLE 1-continued $$\underset{H}{A-N}-\overset{R^1}{\underset{O}{C}}-\overset{B}{\underset{O}{C}}$$ (I-1)

| Comp. No. | A | R¹ | B |
|---|---|---|---|
| 33 | quinoline-2-carbonyl-NH-CH(CH2CONH2)-C(=O)- | benzyl | -NH-CH(iPr)-C(=O)-morpholine (N-methyl) |
| 34 | quinoline-2-carbonyl-NH-CH(CH2CONH2)-C(=O)- | benzyl | -N(CH3)-CH(iPr)-C(=O)-NH-OCH3 |
| 35 | (pyridin-2-yl)CH2-N(CH3)-C(=O)-NH-CH(iPr)-C(=O)- | benzyl | -NH-CH(iPr)-C(=O)-OCH3 |
| 36 | (pyridin-2-yl)CH2-N(CH3)-C(=O)-NH-CH(iPr)-C(=O)- | benzyl | -NH-CH(sec-Bu)-C(=O)-NH2 |
| 37 | (pyridin-2-yl)CH2-O-C(=O)-NH-CH(iPr)-C(=O)- | benzyl | -NH-CH(sec-Bu)-C(=O)-NH2 |
| 38 | (pyridin-2-yl)CH2-O-C(=O)-NH-CH(iPr)-C(=O)- | benzyl | -NH-CH(sec-Bu)-C(=O)-OCH3 |
| 39 | (pyridin-2-yl)CH2-N(CH3)-C(=O)-NH-CH(iPr)-C(=O)- | cyclohexyl | -NH-CH(sec-Bu)-C(=O)-OCH3 |

TABLE 1-continued

Structure (I-1): A-NH-CH(R¹)-[epoxide]-CH₂-C(=O)-B

| Comp. No. | A | R¹ | B |
|---|---|---|---|
| 40 | quinoline-2-carboxamide-Asn | benzyl | N-methyl-(isoleucine)-NHOH |
| 41 | quinoline-2-carboxamide-Asn | benzyl | N-methyl-(valine)-NHOH |
| 42 | quinoline-2-carboxamide-Asn | benzyl | N-methyl-NH-CH(iPr)-CH₂-Ph |
| 43 | " | " | N-methyl-NH-CH(iPr)-Ph |
| 44 | " | " | N-methyl-NH-CH(iPr)-CH₂CH₂-Ph |
| 45 | " | " | N-methyl-NH-CH(iPr)-CH₂CH₂CH₂-Ph |
| 46 | " | " | N-methyl-NH-CH(iPr)-iPr |
| 47 | " | " | N-methyl-NH-CH(iPr)-Ph |

TABLE 1-continued (I-1) structure: A—N(H)—CH(R¹)—...—B with epoxide O and carbonyl O

| Comp. No. | A | R¹ | B |
|---|---|---|---|
| 48 | quinoline-2-carbonyl-NH-CH(CH₂C(O)NH₂)-C(O)- | benzyl (CH₂-phenyl) | N(H)-CH(iPr)-CH₂-phenyl |
| 49 | " | " | N(H)-CH(iPr)-CH₂CH₂-phenyl (with extra CH₂) |
| 50 | " | " | N(H)-CH(iPr)-CH₂CH₂CH₂-phenyl |

The cis-epoxide compounds of formula (I-1) of the present invention may be prepared by using several reaction schemes, as illustrated in the following Schemes 1, 2 and 3. (wherein:

R¹, A and B have the same meanings as defined previously; and

P is an amino protecting group, preferably, a benzyloxycarbonyl group).

As shown in Scheme 1, a coupling reaction of an epoxide compound of formula (II) and a compound of formula (III) is carried out to obtain a compound of formula (IV); and, after removing the protecting group from the compound of formula (IV), another coupling reaction of the compound without the protecting group and a compound of formula (V) is carried out to obtain the desired compound of formula (I-1).

wherein R¹, A, B and P have the same meanings as defined previously.

As shown in Scheme 2, a coupling reaction of a compound of formula (VI) and a compound of formula (III) is carried out to give a compound of formula (VII); the compound of formula (VII) is epoxidized to give a compound of formula (VIII); and after the removal of the protecting group, another coupling reaction of the compound of formula (VIII) without the protecting group and a compound of formula (V) is carried out to give the desired compound of formula (I-1).

wherein R¹, A and B have the same meanings as defined previously; and P is an amino protecting group, preferably, t-butoxy carbonyl group.

As shown in Scheme 3, a coupling reaction of a compound of formula (VI) and a compound of formula (III) is carried out to give a compound of formula (VII); after removing the protecting group from the compound of formula (VII), another coupling reaction of the compound without the protecting group and a compound of formula (V) is carried out to give a compound of formula (IX); and the compound of formula (IX) is epoxidized to give the desired compound of formula (I-1).

The epoxidation reaction in the above Schemes 2 and 3 can be carried out in accordance with a known method by employing metachloroperoxybenzoic acid.

Further, the coupling reagents which can be used for the above coupling reactions in Schemes 1,2 and 3 may include, but are not limited to, dicyclohexyl carbodiimide(DCC), 3-ethyl-3'-(dimethylamino)propylcarbodiimide(EDC), bis-(2-oxo-3-oxazolidinyl)-phosphinic chloride(BOP-Cl), diphenylphosphorylazide(DPPA), and the like.

Alternatively, the coupling reactions may be carried out without any coupling reagent by employing acyl halides or activated ester derivatives. Suitable acyl halides include acyl chlorides; and, suitable activated ester derivatives are those commonly used for activating carboxylic acid groups for coupling with an amine to form an amide bond, or for coupling with an alcohol to form an ester bond including, but not limited to, anhydrides derived from alkoxycarbonyl chlorides such as methoxycarbonyl chloride, isobutoxycarbonyl chloride, and the like, carboxylic acid derived anhydrides, and, esters derived from N-hydroxybenzotriazole, N-hydroxyphthalimide, N-hydroxysuccinimide, N-hydroxy-5-norbornene-2,3-dicarboxamide, 2,4,5-trichlorophenol, and the like.

The removal of the protecting groups may be carried out in accordance with a known method in the art, depending on the kind of the protecting group involved: for instance, a benzyloxy-carbonyl group can be removed in the presence of a Pd/C catalyst under a pressure of hydrogen; and a t-butoxycarbonyl group can be removed by reacting with trifluoroacetic acid.

The compounds of formula (II) and (IV) used in Schemes 1, 2 and 3 are novel compounds, and may be prepared in accordance with the procedures explained hereinbelow.

First, the compound of formula (II) may be prepared in accordance with Scheme 4 given below.
wherein:

$R^1$ has the same meaning as defined previously;

P is an amino protecting group;

P' is an alcohol protecting group; and

X is a halogen such as Cl, Br and I.

As shown in Scheme 4, after protecting the alcohol group of 3-halo-propan-1-ol, the protected compound is reacted with triphenylphosphine to give a phosphonium salt of formula (X); the salt of formula (X) is reacted with an aldehyde of formula (XI) to give a compound of formula (XII); the protecting group P' is removed from the compound of formula (XII), which is then epoxidized by employing the same method as described above to obtain a compound of formula (XIII); and, the alcohol group of the compound of formula (XIII) is oxidized to obtain the desired compound of formula (II).

On the other hand, a compound of formula (VI) may be prepared in accordance with the following Scheme 5.
wherein $R^1$, P and X have the same meanings as defined previously.

The above Scheme 5 is carried out in accordance with a known method(see Keinan et al., Tetrahedron 47, 4631–4638 (1991); Corey & Shimaji, JACS 105, 1662–1664(1983)).

However, if a compound of formula (XIV) is to be reacted with a compound of formula (XI) using $K_2CO_3$ in accordance with the Wittig reaction method described in the above references to obtain a cis-β,γ-olefinic compound of formula (VI), the reaction is supposed to be carried out at a high temperature ranging from 70° to 80° C., which entails racemization at the position of phenylalanal. In the present invention, therefore, the racemization is avoided by way of carring out the Wittig reaction at a low temperature, e.g., –78° C., using potassium hexamethyldisilazane (KHMDS) as a base.

Furthermore, if an orthoester of formula (XV) is acid-treated to give a compound (XVI), which is then base-treated to remove a protecting group, as described in the references, more than 50% of β,γ-olefinic acid will be converted to α,β-olefinic acid; and, consequently, the yield of β,γ-olefinic acid becomes very low. Further, it is difficult to purify β,γ-olefinic acid from the mixture. These problems are overcome in the present invention by way of stirring an orthoester of formula (XV) on heating at a reflux temperature of a solvent(t-butanol, tetrahydrofuran or dioxane may be used.) in the presence of an acid catalyst, e.g., HCl, to give the compound of formula (VI) with a 80–90% yield.

In accordance with the present invention, the functionalized (wherein $R^8$ and $R^9$ have the same meanings as defined previously) may be prepared in accordance with the following Schemes 6 and 7.
(wherein, R is a phenyl, benzyl, 2-phenylethyl or 3-phenylpropyl group; and X is a halogen).

As shown in Scheme 6, the desired amine of the formula (wherein $R^8$ and $R^9$ have the same meaning as defined previously) may be prepared by a Grignard reaction and a reduction reaction with $NaBH_4$ from isobutyro nitrile. Since the intermediate compounds in Scheme 6 are produced as a racemic mixture, after t-butoxycarbonyl-phenylalanine is coupled to the racemic mixture and t-butoxy-carbonyl group is removed therefrom, two diastereomers are separated from each other by way of column chromatography. The separated diastereomers are cleaved by employing Edman method to produce the desired compound.

The following Scheme 7 shows a process for preparing (2S)-amino-1-phenyl-3-methylbutane which is useful for determining the stereochemistry of 2-amino-1-phenyl-3-methylbutane prepared in accordance with Scheme 6.

As shown in Scheme 7, an ethoxycarbonyl group is introduced to D-valine; and, thereafter, benzene is introduced to the carbonyl group in the valine through Friedel-Crafts reaction to prepare a compound of formula (XVII). A ketone group in the compound of formula (XVII) is reduced to an alcohol group by employing $NaBH_4$; the ethoxycarbonyl group is removed from the resulting compound; and the alcohol group is removed therefrom by way of bromination with $PBr_5$ followed by hydrogenation with Pd/C catalyst to produce (2S)-amino-1-phenyl-3-methylbutane.

This compound is used as a standard compound of (S) form to determine the stereochemistry of the compounds produced by Scheme 6; and it is found that the compound eluted earlier during column chromatography in Scheme 6 is of S(–) form, and that the compound eluted later in Scheme 6 is in R(+) form.

On the other hand, a compound of formula (I-2) of the present invention may be prepared in accordance with the following Schemes 8 and 9.
(wherein, $R^{10}$, $R^{11}$, D and E have the same meanings as defined previously; P is an amino protecting group, preferably, t-butoxycarbonyl group; Me represents a methyl group; DIBAL represents diisobutylaluminium hydride; Ph is a phenyl group; and mCPBA means metachloroperoxybenzoic acid).

In accordance with Scheme 8, a compound of formula (XVIII) is esterified by a conventional method to obtain a compound of formula (XIX), which is then reduced by employing diisobutyl-aluminium hydride to obtain a compound of formula (XX); and, the compound of formula (XX) is reacted with a triphosphonium salt of formula (XXI) through a Wittig reaction to obtain a compound of formula (XXII), preferably in the presence of a base, e.g., n-butyllitium, potassium carbonate, dimethylsulfoxide anion, etc. After removing the protecting group from the compound of formula (XXII), the compound so obtained is reacted with a compound of formula (XXIII) for amide-coupling to obtain a compound of formula (XXIV), wherein a coupling reagent conventionally used in the art, preferably, dicyclohexylcarbodiimide(DCC) or 3-ethyl-3'-(dimethylamino)propylcarbodiimide(EDC), may be employed; and, then, the compound of formula (XXIV) is epoxidized in metachloroperoxybenzoic acid to obtain the desired compound of formula (I-2).

(wherein, $R^{10}$, $R^{11}$, D, E and mCPBA have the same meanings as defined previously; and P is an amino protecting group, preferably, a benzyloxycarbonyl group).

In accordance with Scheme 9, the compound of formula (XXII) obtained by the same method as described in Scheme 8 is epoxidized to give a compound of formula (XXV); after the removal of the protecting group from the compound of formula (XXV), the compound so obtained is reacted with a compound of formula (XXIII) for amide coupling to obtain the desired compound of formula (I-2), wherein the epoxidization and the amide coupling are carried out under the same conditions as those in Scheme 8.

In the case that both p and q are 1, the amide coupling in Scheme 9 can be carried out in two steps as shown in the following Scheme 10.
(wherein, $R^{10}$, $R^{11}$, $R^{15}$, $R^{16}$, D and E have the same meanings as defined previously; and, P and P'' are respectively an amino protecting group, preferably, a benzyloxycarbonyl group.)

Specifically, after the removal of the protecting group P from the compound of formula (XXV), the resulting compound is reacted with a compound of (XXVI) for amide coupling to obtain a compound of formula (XXVII); and, after the removal of the protecting group P" from the compound of formula (XXVII), the resulting compound is reacted with a carboxylic acid of formula (XXVIII) or an acyl chloride of formula (XXIX) for amide coupling to obtain the compound of formula (I-2) wherein both p and q are 1, and the coupling reaction conditions are the same as those described above.

Further, compounds of formula (I-3) and intermediate compounds of formula (XXX) or (XXXI) may be prepared as shown in Schemes 11 to 13 given hereinbelow.

(wherein $R^1$, K, G, Q, r and J have the same meanings as defined previously; and Z represents a benzyloxycarbonyl group.)

(wherein $R^1$, K, G, Q, r and J have the same meanings as defined previously; and Z' represents a t-butoxycarbonyl group.)

(wherein $R^1$, Z and Z' have the same meanings as defined above; and P is an amino protecting group.)

Schemes 11 and 12 describe processes for preparing the desired compound of formula (I-3) through amide coupling and epoxidation reactions.

Scheme 11 shows the process for preparing the compound of formula (I-3) wherein K—G and Q—(J), are an equal group. Specifically, a compound of formula (XXX) is converted to a diamine of formula (a) by the removal of the protecting group in the presence of Pd/C catalyst under a pressure of hydrogen; and the diamine of formula (a) is reacted with 2 equivalents of K—G—OH for coupling to obtain the desired compound of formula (I-3).

As shown in Scheme 12, in the case that K—G and Q—(J), are different from each other, an intermediate compound of formula (XXXI) is first reacted with HO—Q—(J), for amide coupling to obtain a compound of formula (b), from which the protecting group is removed by employing an acid such as trifluoroacetic acid; and the resulting compound is reacted with K—G—OH for amide coupling to obtain a compound of formula (d). The compound of formula (d) is epoxidized with methachloroperbenzoic acid to obtain the desired compound of formula (I-3).

Further, the above coupling reactions in Scheme 12 may be carried out by employing the coupling reagents as described in Schemes 2 and 3; and the carboxylic acids subject to the amide coupling reactions may be first reacted with acyl halide derivatives or activated ester derivatives for coupling reactions without using any coupling reagent, as described in Schemes 2 and 3.

In Scheme 13, there is presented a process to prepare compounds of formulae (XXX) and (XXXI) to be used as intermediates for preparing the compounds of the present invention: that is, N-(2-bromoethyl)phthalate is reacted with triphenylphosphine; the resulting compound is then Wittig-reacted with an aldehyde compound derived from an amino acid having a N-protecting group to obtain a cis-olefinic compound. Subsequently, phthalimide in the cis-olefinic compound is removed by employing hydrazine, whereby the compound of formula (XXXI), the starting material in Scheme 12, is obtained if P is Z', i.e., t-butoxycarbonyl; and, if P is Z, i.e., benzyloxycarbonyl, it is further introduced to the free amino group, and the resulting compound is epoxidized to obtain the compound of formula (XXX), the starting material for Scheme 11.

The compounds of the present invention may have one or more asymmetric carbons; and, therefore, the present invention encompasses, within its scope, racemic mixtures, mixtures of diastereomers, as well as single diastereomers which can be collectively represented by the formulae (I-1) to (I-3).

Furthermore, the present invention encompasses, within its scope, those pharmaceutically acceptable non-toxic salts, solvates and hydrates of the compounds of formulae (I-1) to (I-3).

Suitable pharmaceutically acceptable salts of the compounds of formulae (I-1) to (I-3) are conventional non-toxic salts and may include inorganic salts, for example, metal salts such as alkali metal salts(e.g., sodium salt, potassium salt, etc.), and alkaline earth metal salts(e.g., calcium salt, magnesium salt, etc.), ammonium salts, etc.; organic salts, for example, organic amine salts(e.g., trimethylamine salt, N-methylglucamine salt, diethanolamine salt, triethanolamine salt, triethylamine salt, pyridine salt, procaine salt, picoline salt, dicyclohexylamine salt, N,N'-dibenzylethylene-diamine salt, tris(hydroxymethylamino) methane salt, phenylethylbenzylamine salt, dibenzylethylenediamine salt, etc.); organic carboxylic or sulfonic acid salts (e.g., formate, acetate, maleate, tartrate, methanesulfonate, benzenesulfonate, toluenesulfonate, etc.); inorganic acid salts(e.g., hydrochloride, hydrobromide, sulfate, phosphate, etc.); salts with basic or acidic amino acids(e.g., arginine, aspartic acid, glutamic acid, lysine, etc.); more preferably, alkali metal salts, alkaline earth metal salts, inorganic acid salts, organic carboxylic acid salts and salts with basic or acidic amino acids; and most preferably, sodium salts, potassium salts, hydrochlorides and sulfates.

Above pharmaceutically acceptable non-toxic salts may be prepared by reacting the compounds of the formulae (I-1) to (I-3) with one to four equivalents of corresponding acids or bases to the salts mentioned above in the Presence of a solvent which may be water, or a mixture of water and water-miscible solvent(e.g., methanol, ethanol, acetonitrile, acetone, etc).

Exemplary solvates of the compounds of formulae (I-1) to (I-3) may include solvates with water-miscible solvents, preferably, ethanol, which may be prepared by employing a conventional method, for example, as described in Techniques of Solubilization of Drugs, ed. by Yalkowsky(1981), Marcel Dekker Inc. New York.

The hydrates of the compounds of formulae (I-1) to (I-3) may be prepared by employing a known method, for example, as described in Techniques of Solubilization of Drugs, ed. by Yalkowsky(1981), Marcel Dekker Inc. New York.

The compounds of the present invention may be used for the treatment or prophylaxis of diseases caused by HIV, including AIDS. Accordingly, the present invention includes pharmaceutical compositions which contain, in addition to non-toxic, inert pharmaceutically suitable carriers, one or more compounds of the invention. In general, it is advantageous both in human and veterinary medicine to administer the active compound or compounds of the invention in total amounts of about 0.001~10 mg/kg of body weight every 24 hours, if appropriate, in the form of several individual dosages, to achieve desired results. However, it may be necessary to deviate from the amounts mentioned and in particular to do so as a function of the nature and body weight of the subject to be treated, the nature and severity of the disease, the nature of formulation and administration of the medicament and the interval within which the administration takes place.

The composition of the present invention may be administered orally or by injection. These compositions may be in the form of tablets, capsules, pills, granules, solutions, emulsions, suspensions and the like.

Solutions, emulsions and suspensions may be prepared by using a conventional method. Solutions and emulsions may contain, in addition to the active compound or compounds of the invention, customary carriers or excipients, such as solvents, solubilizing agents and emulsifiers, for example, water, ethyl alcohol, isopropyl alcohol, propylene glycol, oils. Suspensions can contain, in addition to the active compound, customary carriers or excipients, such as liquid diluents, for example, water, ethyl alcohol or propylene glycol and suspending agents, for example, ethoxylated isostearyl alcohol, polyoxyethylene sorbitol and sorbitan esters, microcrystalline cellulose and aluminum metahydroxide, or mixtures of these substances.

Solid compositions for oral administration may include an inert diluent such as sucrose, lactose, etc. and a lubricant such as magnesium stearate. The compound of the present invention may be administered simultaneously with one or more other anti-AIDS agents or immunomodulators.

The following Preparation Examples and Examples are provided for purposes of illustrating certain aspects of the present invention only; and are not to be construed as limiting the scope of the present invention in any way.

The terms and abbreviations used in the Examples have their normal meaning unless otherwise designated, for example, "° C." refers to degrees Celsius; "N" refers to normal or normality; "mmol" refers to millimole; "g" refers to gram; "ml" means milliliter; "M" refers to molar; "NMR" refers to nuclear magnetic resonance; "FABMS" refers to fast atomic bombardment mass spectrometry; "IR" refers to infrared (spectrophotometry); "v/v" means volume per volume; "w/v" refers to weight per volume; and "w/w" means weight per weight.

Unless otherwise specified, percentages or ratios given below for solids in solid mixtures, liquids in liquids and solids in liquids are on a w/w, v/v and w/v basis, respectively.

PREPARATION EXAMPLE 1

Preparation of 2-amino-3-methyl-1-phenylbutane 1-1) Preparation of 2-amino-3-methyl-1-phenylbutane hydrochloride To a solution of 13.8 g(0.2 mol) of isobutyronitrile dissolved in 50 ml of absolute tetrahydrofuran(THF) was added 2.0M solution of benzyl magnesium chloride(110 ml, 0.22 mol) at room temperature. The reaction mixture was refluxed for 1 hour and then cooled to room temperature. 200 ml of methanol and 11.4 g(0.3 mol) of NaBH$_4$ were added to the resulting solution and the whole mixture was stirred at room temperature for 1 hour. The reaction was quenched by adding 300 ml of 1N hydrochloric acid and the solvent was removed by distillation under a reduced pressure. The reaction mixture was adjusted to pH 11 with 1N NaOH solution, extracted with chloroform, dried over anhydrous Na$_2$SO$_4$, and 50 ml of 5N hydrochloric acid in methanol was added thereto. The resulting solution was purified by column chromatography using dichloromethane: methanol(10:1) as an eluent to give 37.5 g of the title compound(yield:94%).

$^1$H NMR(CDCl$_3$) δ 1.08(m, 6H), 1.96(m, 1H), 2.90–3.16 (m, 2H), 3.37(m, 1H), 7.15–7.31(m, 5H), 8.36(b, 3H)

1-2) Preparation of L-(N-t-butoxycarbonyl)-phenylalaninyl-2-(1-phenyl-3-methyl-butyl)amide A mixture of 26.5 g(0.1 mol) of N-t-butoxycarbonylphenylalanine and 1.5 equivalent of each 3-ethyl-3'-(dimethylamino)propyl carbodiimide(EDC) and N-hydroxybenzotriazol(HOBT) was dissolved in a mixture of dimethyl formamide(DMF)(130 ml) and triethylamine(15 ml). 20 g(0.1 mol) of the compound obtained in Preparation Example 1-1) was added to the reaction mixture at 0° C. and the whole mixture was stirred at room temperature for 5 hours. The solvent was removed by distillation under a reduced pressure; and the resulting residue was dissolved in 300 ml of ethyl acetate and then washed with 500 ml of 1N hydrochloric acid and 500 ml of saturated NaHCO$_3$ solution. The organic layer was dried over anhydrous MgSO$_4$ and the solvent was removed to give 37.7 g of the title compound (yield: 92%).

1-3) Preparation of L-phenylalaninyl-2-(1-phenyl-3-methylbutyl)amide 20.5 g(0.05 mol) of the title compound of the Preparation Example 1-2) was dissolved in a mixture of dichloromethane (30 ml) and trifluoroacetic acid(15 ml) and the reaction mixture was stirred at room temperature for 1 hour. Thereafter, the mixture was distilled under a reduced pressure to remove the solvent; and, the residue was purified by column chromatography using ethyl acetate as an eluent to isolate two isomers.

8.0 g(R$_f$:0.50) and 7.4 g(R$_f$:0.45) of two isomers were obtained respectively, and the total yield was 99%.

$^1$H NMR(CDCl$_3$)δ

R$_f$=0.50 0.93(m, 6H), 1.80(m, 1H), 2.22(m, 1H), 2.63(m, 1H), 2.85(m, 1H), 3.05(m, 1H), 3.51(m, 1H), 4.11(m, 1H), 7.10–7.34(m, 10H)

R$_f$=0.45 0.91(m, 6H), 1.79(m, 1H), 2.65–2.70(m, 2H), 2.83 (m, 1H), 3.18(m, 1H), 3.44(m, 1H), 4.08(m, 1H), 7.10–7.32(m, 10H)

1-4) Preparation of 2-amino-3-methyl-1-phenylbutane

Each 1.46 g(4.7 mmol) of the two isomers obtained in Preparation Example 1-3) was dissolved in 50 ml of dry dichloromethane, and 0.66 ml(5.5 mmol) of phenylisothiocyanate was added thereto at room temperature, respectively. Each of the reaction mixtures was refluxed for 2 hours, cooled to room temperature and then 10 ml of trifluoroacetic acid was added thereto. Each of the resulting solutions was refluxed at 60° C. for 40 minutes and then the solvent was removed by distillation under a reduced pressure. Each residue was dissolved in 20 ml of water and washed with ether, and then the solution was adjusted to pH 11 with 2N NaOH and extracted with chloroform to give the title compound(yield: 82 to 85%).

$^1$H NMR(CDCl$_3$) δ 0.94(m, 6H), 1.11(bs, 2H), 1.65(m, 1H), 2.39(m, 1H), 2.82(m, 2H), 7.16–7.32(m, 5H)

[α]$_D$ (1) −38.1(C=0.12, dichloromethane)

[α]$_D$ (2) +38.1(C=0.12, dichloromethane)

PREPARATION EXAMPLE 2

Preparation of (S)-2-amino-3-methyl-1-phenylbutane 2-1) Preparation of [(ethoxycarbonyl)amino]-3-methyl-1-phenyl-butan-2-one To a solution of 9.45 g(0.05 mol) of D-(N-ethoxycarbonyl)valine dissolved in 150 ml of dry dichloromethane were added 0.25 ml of dimethylformamide and 50 ml(0.053 mol) of oxalylchloride at 0° C. under nitrogen atmosphere, and the reaction mixture was stirred at room temperature for 2 hours. After the addition of 70 ml of dry dichloromethane and 650 ml of dry benzene to the reaction mixture, 14.2 g(0.105 mol) of aluminium trichloride was added thereto at −15° C. The whole mixture was stirred at the same temperature for 14 hours, and then the reaction was quenched with 150 ml of 1N hydrochloric acid and 150 ml of water. The organic layer was separated and washed successively with 1N hydrochloric acid, water and saturated NaHCO$_3$ solution and then dried over anhydrous MgSO$_4$. The residue was purified by column chromatography using ethyl acetate:hexane(5:95) as an eluent to give 10.8 g of the title compound(yield: 87%).

$^1$H NMR(CDCl$_3$) δ 0.71(d, 3H), 0.99(d, 3H), 1.18(t, 3H), 2.10(m, 1H), 4.02(m, 2H), 5.22(m, 1H), 5.71 (d, 1H), 7.35–7.55(m, 3H), 7.92(d, 2H)

2-2) Preparation of (S)-2-amino-3-methyl-1-phenylbutane

To a methanolic solution(150 ml) of 10 g(0.04 mol) of the title compound obtained in Preparation Example 2-1) was added 2.3 g(0.06 mol) of sodium borohydride slowly, and the mixture was stirred at room temperature for 1 hour. The reaction was quenched with the addition of 10 ml of acetic acid, and methanol was removed by distillation under a reduced pressure. The resulting solution was diluted with 200 ml of saturated NaHCO$_3$ solution and extracted with dichloromethane(2×100 ml). The organic solvent was removed by distillation under a reduced pressure and the residue was dissolved in 160 ml of methanol:water(3:1(v/v)). To the resulting solution was added 5.6 g(0.1 mol) of potassium hydroxide and the whole mixture was refluxed for 3 hours. The solvent was removed by distillation under a reduced pressure and the residue was diluted with 20 ml of water, acidified with 1N phosphoric acid and washed with ether(3×50 ml). The aqueous layer was adjusted to pH 11 with 2N NaOH and extracted with dichloromethane(4×100 ml), and then 10 ml of 5N hydrochloric acid in methanol was added thereto. The solvent was removed by distillation under a reduced pressure and the residue was dissolved in 200 ml of dioxane. To the resulting solution was added 17.3 g(0.04 mol) of PBr$_5$, and then the whole mixture was stirred at 95° C. for 2 hours. The solvent was removed by distillation under a reduced pressure; and, the residue was dissolved in 200 ml of ethanol at 0° C. 2 g of 10% Pd/C was added to the resulting solution and the mixture was stirred for 8 hours under hydrogen atmosphere(55 psi). The reaction mixture was passed through Celite to remove Pd/C, and the solvent was removed by distillation under a reduced pressure. The residue was extracted with 100 ml of 1N NaOH and dichloromethane(3×100 ml); and, the organic solvent was removed therefrom to give 5.15 g of the title compound (yield: 79%).

$[α]_D$=−37.0(C=0.12, dichloromethane)

PREPARATION EXAMPLE 3

Preparation of 5-L-(N-benzyloxycarbonyl)amino-6-phenyl-hex-3-(cis)-ene-1-carboxylic acid 3-1) Preparation of 5-L-(N-benzyloxycarbonyl)amino-6-phenyl-hex-3-(cis)-enyl-4'-methyl-2',6',7'-trioxa-bicyclo[2',2'.2'] oxetane 60.8 g(0.12 mol) of 1-(2-triphenylphosphonium-methyl)-4'-methyl-2',6',7'-trioxa-bicyclo[2',2'.2']oxetane bromide prepared according to the method described by Keinan et al. in Tetrahedron 26, 4631–4638(1991) was dissolved in 400 ml of tetrahydrofuran and the mixture was stirred at −78° C. for 10 minutes. Then, 220 ml(0.11 mol) of 0.5M potassium hexamethyldisilazane was added thereto and the whole mixture was stirred at −78° C. for 1 hour. To the mixture was added a solution of 30 g (0.106 mol) of L-(N-benzyloxycarbonyl)phenylalaninal dissolved in 150 ml of tetrahydrofuran and cooled to −78° C., slowly over 40 minutes; the whole mixture was stirred at −78° C. for 1 hour and subsequently at room temperature for 1 hour; and then, the reaction was quenched with water. The solvent was removed from the reaction mixture and the residue was dissolved in 500 ml of dichloromethane and washed with saturated NaHCO$_3$ solution and water. The organic layer was dried over anhydrous Na$_2$SO$_4$ and the residue was purified by column chromatography using hexane:ethylacetate:triethylamine (70:25:5) as an eluent to give 36.5 g of the title compound (yield: 84%).

$^1$H NMR(CDCl$_3$) δ 0.8(s, 3H), 2.2–3.0(m, 4H), 3.9(s, 6H), 4.6(m, 1H), 4.8(br, 1H), 5.05(s, 2H), 5.4–5.6(m, 2H), 7.1–7.5(m, 10H)

3-2) Preparation of 5-L-(N-benzyloxycarbonyl)amino-6-phenyl-hex-3-(cis)-ene-1-carboxylic acid 2.5 g(6 mmol) of the compound obtained in Preparation Example 3-1) was dissolved in a mixture of water(12 ml) and t-butanol(60 ml) containing less than 5% of conc. hydrochloric acid, and the resulting solution was refluxed at the reflux temperature of the solvent for 20 hours. The solvent was removed from the solution by distillation under a reduced pressure and the residue was adjusted to pH 10 with saturated K$_2$CO$_3$ solution and then washed three times with each 300 ml of dichloromethane. The organic layer was removed and the aqueous layer was adjusted to pH 2, extracted with ethyl acetate, dried over anhydrous MgSO$_4$. Evaporation of the organic solvent under a reduced pressure gave 1.62 g of the title compound(yield: 80%).

$^1$H NMR(CDCl$_3$) δ 2.7–3.3(m, 4H), 4.6(m, 1H), 4.8(br, 1H), 5.05(s, 2H), 5.4(t, 1H), 5.6(m, 1H), 7.1–7.3 (m, 10H)

Mass(FAB, m/e) 340(M+1)

$[α]_D$ =+25.2(C=0.50, methanol)

PREPARATION EXAMPLES 4 TO 7

The same procedures as described in Preparation Example 1 were repeated using phenyl magnesium chloride, 2-phenylethyl magnesium chloride, 2-phenylethyl magnesium bromide, 3-phenylpropyl magnesium bromide and methyl magnesium chloride, respectively, in place of benzyl magnesium chloride to obtain functionalized amines. Each compound obtained in Preparation Examples 4 to 7 and physical properties thereof are given below in table 4.

PREPARATION EXAMPLE 8

Preparation of N-[5-L-(N-benzyloxycarbonyl)-(4R, 3S)-epoxy-6-phenylhexanoyl]-L-isoleucine methyl ester 8-1) Preparation of N-[5-L-(N-benzyloxycarbonyl)amino-6-phenyl-hex-3-(cis)-en-1-oyl]-isoleucine methyl ester 339 mg(1 mmol) of the compound obtained in Preparation Example 3 was dissolved in dry dichloromethane and 1 equivalent of isoleucine methyl ester and 4 equivalents of triethylamine were added thereto. The whole mixture was cooled to 0° C. and 1.5 equivalent of POCl$_3$ was added dropwise to the mixture slowly. After 3 hours, the resulting solution was diluted with the addition of dichloromethane and washed with basic water. The organic layer was dried over anhydrous MgSO$_4$ and distilled under a reduced pressure to remove the solvent. Then, the residue was purified by column chromatography using hexane:ethyl acetate(7:3) as an eluent to give 256 mg of the title compound(yield: 55%).

$^1$H NMR(CDCl$_3$) δ 0.9(m, 6H), 1.1–1.4(m, 2H), 1.8(m, 1H), 2.6–2.9(m, 3H), 3.2(m, 1H), 3.7(s, 3H), 4.4–4.6(m, 2H), 4.8–5.1(m, q, 3H), 5.4 (d, 1H), 5.6(m, 1H), 6.8(m, 1H), 7.1–7.4 (m, 10H)

8-2) Preparation of N-[5-L-(N-benzyloxycarbonylamino)-(4R,3S)-epoxy-6-phenyl-hexanoyl]-L-isoleucine methyl ester To a dichloromethane solution(20 ml) of 256 mg(5.5 mmol) of the compound obtained in Preparation Example 8-1) was added 2 equivalents of 50% metachloroperoxybenzoic acid(MCPBA) and the mixture was stirred for 20 hours. The reaction mixture was washed successively with 30 ml of Na$_2$S$_2$O$_3$ solution and 30 ml of saturated NaHCO$_3$ solution. The organic layer was dried over anhydrous MgSO$_4$ and the organic solvent was removed by distillation under a reduced pressure. The residue was purified by column chromatography using hexane:ethyl acetate (1:1) as an eluent to give 212 mg of the title compound(yield: 80%).

$^1$H NMR(CDCl$_3$) δ 0.9(m, 6H), 1.1–1.4(m, 2H), 1.8–2.3 (m, 3H), 2.7–3.4(m, 4H), 3.7(s, m, 4H), 4.6(m, 1H), 5.1(br s, 3H), 6.3(br, 1H), 7.1–7.5(m, 10H)

Mass(FAB, m/e) 483(M+1)

PREPARATION EXAMPLE 9

Preparation of 5-L-(N-benzyloxycarbonylamino)-6-phenyl-hex-(4R,3S)-epoxy-1-carboxylic acid 9-1) Preparation of 2-[5-L-(N-benzyloxycarbonylamino)-6-phenyl-hex-3-(cis)-ene-1-oxy]-tetrahydropyrane 3.4 g(11 mmol) of N-benzyloxycarbonyl-phenylalanal, 7.5 g (16.5 mmol) of 2-(3-triphenylphosphonium-3-propane-1-oxy)tetrahydropyrane iodide and 4.5 g(33 mmol) of K$_2$CO$_3$ were dissolved in 150 ml of 1,4-dioxane, and the mixture was refluxed for 20 hours. The reaction mixture was cooled, diluted with 50 ml of ethyl acetate and then washed with water. The organic layer was dried over anhydrous MgSO$_4$ and removed by distillation under a reduced pressure. The residue was purified by column chromatography using hexane:ethyl acetate (8:2) as an eluent to give 4.2 g of the title compound(yield: 93%), which contains both cis-olefin and trans-olefin in a ratio of 6:1.

$^1$H NMR(CDCl$_3$) δ 1.4–1.7(m, 6H), 2.1(m, 2H), 3.6–3.9 (m, 2H), 3.1(m, 1H), 3.4(m, 1H), 3.5(m, 1H), 3.7(m, 1H), 4.4(s, 1H), 5.0(s, 2H), 5.2(m, 1H), 5.4(m, 1H), 7.1–7.4(m, 10H)

Mass(FAB, m/e) 410(M+1)

9-2) Preparation of 5-L-(N-benzyloxycarbonyl)amino-6-phenyl-hex-3-(cis)-ene-1-ol To an ethanolic solution(450 ml) of 12 g(20 mmol) of the compound obtained in Preparation Example 9-1) was added 1.2 g of pyridinium-para-toluenesulfonate(PPTS), and the mixture was stirred at 70° C. for 6 hours. The solvent was distilled off under a reduced pressure and the residue was purified by column chromatography using hexane:ethyl acetate(8:2) as an eluent to give 7.3 g(yield: 75%) of the titled cis-olefin compound and additional 1.2 g(yield: 12%) of trans-olefin compound.

$^1$H NMR(CDCl$_3$) δ 2.0–2.4(m, 2H), 3.6–3.9(m, 2H), 3.5(m, 2H), 4.5(m, 1H), 5.0(m, s, 3H), 5.3–5.5(m, 2H), 7.1–7.4(m, 10H)

9-3) Preparation of 5-L-(N-benzyloxycarbonyl)amino-6-phenyl-(4R,3S)-epoxy-hexan-1-ol 4 g of the compound obtained in Preparation Example 9-2) and 10 g of metachloroperbenzoic acid were dissolved in 300 ml of dichloromethane and the mixture was stirred at room temperature for 10 hours. To the mixture was added 5 g of Na$_2$S$_2$O$_3$ and stirred for further 30 minutes. The mixture was extracted with ethyl acetate and saturated aqueous NaHCO$_3$ solution. The organic layer was dried over anhydrous MgSO$_4$ and distilled under a reduced pressure to give 3.89 g of the title compound(yield: 90%).

$^1$H NMR(CDCl$_3$) δ 1.3–1.6(m, 2H), 2.8–3.1(m, 4H), 3.7(t, 2H), 3.8(m, 1H), 5.0(br, 1H), 5.1(s, 2H), 7.2–7.4 (m, 10H)

Mass(FAB, m/e) 342(M+1)

9-4) Preparation of 5-L-(N-benzyloxycarbonylamino)-6-phenyl-hex-(4R,3S)-epoxy-1-carboxylic acid To a DMF solution(6 ml) of 324 mg(1 mmol) of the compound obtained in Preparation Example 9-3) was added 2.5 g(6.6 mmol) of pyrimidium dichromate and the mixture was stirred at room temperature for 100 hours under nitrogen atmosphere. The reaction mixture was filtered through Celite and the filtrate was concentrated under a reduced pressure. The residue was taken up in 50 ml of ethylacetate and washed with 50 ml of 1M KHSO$_4$ solution. The organic layer was dried over anhydrous MgSO$_4$ and distilled under a reduced pressure to give 280 mg of the title compound (yield: 80%).

$^1$H NMR(CDCl$_3$) δ 2.0(m, 2H), 2.8–3.1(m, 3H), 3.3(m, 1H), 3.6(m, 1H), 5.1(s, 2H), 5.9(d, 1H), 7.1–7.4 (m, 10H)

Mass(FAB, m/e) 356(M+1)

PREPARATION EXAMPLE 10

Preparation of N-[5-L-(N-benzyloxycarbonylamino)-(4R,3S)-epoxy-6-phenyl-hexanoyl]-L-isoleucinyl-N-methoxy-amine 10-1) Preparation of L-(N-benzyloxycarbonyl)-isoleucinyl-N-methoxy amine 2.63 g(10 mmol) of L-(N-benzyloxycarbonyl)-isoleucine, 493.5 mg(10.5 mmol) of purified N-methoxyamine, 2.3 g(12 mmol) of 3-ethyl-3'-(dimethylamino)-propyl carbodiimide (EDC) and 1.75 g (13 mmol) of 1-hydroxybenzotriazol hydrate were dissolved in 15 ml of dry dimethylformamide and the mixture was stirred for 6 hours under nitrogen atmosphere. The solvent was removed by distillation under a reduced pressure and the residue was dissolved in 100 ml of dichloromethane and washed with 200 ml of brine. The organic layer was dried over anhydrous MgSO$_4$ and distilled under a reduced pressure to give 2.48 g of the title compound (yield: 85%).

$^1$H NMR(CDCl$_3$) δ 0.9(m, 6H), 1.0–2.0(m, 3H), 3.8(s, 3H), 4.3 (m, 1H), 4.8(d, 1H), 5.0(s, 2H), 7.1–7.5 (m, 5H), 8.5(d, 1H)

10-2) Preparation of 5-L-(N-benzyloxycarbonyl)amino-6-phenyl-hex-3-(cis)-en-1-oyl-isoleucinyl-N-methoxy amine To a methanolic solution(30 ml) of 584 mg(2 mmol) of the product obtained in Preparation Example 10-1) was added 60 mg of 10% Pd/C and the mixture was stirred under 1 atmosphere of hydrogen. After 3 hours, the reaction solution was passed through Celite to remove inorganic metals. After the removal of reaction solvent(methanol), 843 mg(2.2 mmol) of EDC hydrochloride, 675 mg(2.5 mmol) of 1-hydroxybenzotriazol hydrate and 678 mg (2 mmol) of the compound obtained in Preparation Example 3-2) were mixed together and the mixture was stirred for 6 hours in dry dimethylformamide solution. After removing the solvent by distillation under a reduced pressure, the residue was dissolved in 50 ml of dichloromethane and washed with 50 ml of saturated NaHCO$_3$ solution. The organic layer was dried over anhydrous MgSO$_4$ and concentrated under a reduced pressure. The residue was purified by column chromatography using hexane:ethyl acetate(6:4) as an eluent to give 420 mg of the title compound having cis configuration only(yield: 43.6%).

$^1$H NMR(CDCl$_3$) δ 0.9(m, 6H), 1.0–2.0(m, 3H), 2.2–3.2 (m, 4H), 3.8(s, 3H), 4.1(m, 1H), 4.4(m, 1H), 4.8–5.1 (m, s, 3H, NH), 5.2(t, 1H), 5.4(m, 1H), 6.2(m, 1H, NH), 7.1–7.5 (m, 10H), 7.8(d, 1H, NH)

10-3) Preparation of N-[5-L-(N-benzyloxycarbonylamino)-(4R,3S)-epoxy-6-phenyl-hexanoyl]-L-isoleucinyl-(N-methoxy)-amine To a dichloromethane solution(30 ml) of 350 mg(7.2 mmol) of the product obtained in Preparation Example 10-2) was added 3 equivalents of 3-chloroperoxybenzoic acid and the mixture was stirred under reflux for 5 hours. 10 ml of 10% $Na_2S_2O_3$ solution was added thereto, and the whole mixture was stirred for 30 minutes and washed with 50 ml of $NaHCO_3$ solution. The organic layer was dried over $MgSO_4$ and concentrated in vacuo to give 350 mg of the title compound(yield: 70.4%)

$^1H$ NMR($CDCl_3$) δ 0.9(m, 6H), 1.0–2.0(m, 3H), 2.1–3.4 (m, 6H), 3.8(s, 3H), 4.0(m, 1H), 4.4(m, 1H), 4.9(d, 1H, NH), 5.1(s, 2H), 6.2(d, 1H, NH), 7.1–7.5 (m, 10H), 7.8(d, 1H, NH)

Mass(FAB, m/e) 498(M+1)

PREPARATION EXAMPLE 11

Preparation of N-[5-L-(N-benzyloxycarbonylamino)-(4R,3S)-epoxy-6-phenylhexanoyl]-L-isoleucinyl methylamide 11-1) Preparation of L-(N-benzyloxycarbonyl)-isoleucineamide To a pre-cooled solution(−20° C.) of 2.63 g(10 mmol) of L-(N-benzyloxycarbonyl)-isoleucine in 100 ml of dichloromethane were added 1.40 ml of triethylamine and 1.23 ml of pivaloyl chloride successively. After 30 minutes, ammonia gas was bubbled through the reaction mixture for 30 minutes. The resulting precipitate was filtered and the solid was washed with 50 ml of dichloromethane. The combined solution was washed successively with 2N HCl solution(50 ml×2) and 50 ml of brine. The organic layer was dried over anhydrous $MgSO_4$ and concentrated in vacuo to give 2.49 g of the title compound (yield: 95%).

$^1H$ NMR($CDCl_3$) δ 0.9(m, 6H), 1.2(m, 1H), 1.5(m, 1H), 1.8(m, 1H), 4.0(m, 1H), 5.1(s, 2H), 6.5(d, 1H)

11-2) Preparation of L-(N-benzyloxycarbonyl)-isoleucine methylamide

To a pre-cooled solution(−15° C.) of 2.65 g(10 mmol) of L-(N-benzyloxycarbonyl)-isoleucine in 150 ml of dry dichloromethane were added 1.53 ml(11 mmol) of triethylamine and 1.35 ml(11 mmol) of pivaloyl chloride successively. After 30 min., methylamine gas was bubbled through the reaction mixture for an hour. The reaction mixture was diluted with dichloromethane(200 ml) and the resulting solution was washed successively with water, 10% citric acid solution and brine. The organic layer was dried over anhydrous $MgSO_4$ and concentrated under a reduced pressure to give 2.05 g of title compound(yield: 73%).

$^1H$ NMR($CDCl_3$) δ 0.9(m, 6H), 1.0–2.02(m, 3H), 2.8(s, 1H), 3.9(m, 1H), 5.0(s, 2H), 5.3(d, 1H), 7.2–7.5(m,5H)

11-3) Preparation of 5-L-(N-benzyloxycarbonyl)amino-6-phenyl-hex-3-(cis)-en-1-oyl isoleucine methylamide 350 mg(1.2 mmol) of the product obtained in Preparation Example 11-2) was subjected to the removal of N-benzyloxycarbonyl group according to the method of Preparation Example 10-2), and then the same reaction procedures as described in Preparation Example 10-2) were repeated using 407 mg(1.2 mmol) of the product obtained in Preparation Example 3-2). The resulting product was purified by column chromatography to give 370 mg of the title compound(yield: 63%).

$^1H$ NMR($CDCl_3$) δ 0.9(m, 6H), 1.0–2.0(m, 3H), 2.6–3.0 (m, 7H), 4.2(m, 1H), 4.6(m, 1H), 5.0(m, 3H), 5.3–5.7 (m, 2H), 6.0–7.0(m, 2H), 7.1–7.4(m, 10H)

11-4) Preparation of N-[5-L-(N-benzyloxycarbonylamino)-(4R,3S)-epoxy-6-phenyl hexanoyl]-L-isoleucinyl methylamide The same procedures as described in Preparation Example 10-3) were repeated using 370 mg(0.79 mmol) of the product obtained in Preparation Example 11-3) to give 300 mg of the title compound(yield: 78%).

$^1H$ NMR($CDCl_3$) δ 0.9(m, 6H), 1.0–2.0(m, 3H), 2.6–3.2 (m, 9H), 4.3(m, 2H), 5.0(m, 3H), 6.0–7.0(m, 2H), 7.1–7.4 (m, 10H)

PREPARATION EXAMPLE 12

Preparation of N,N-(2-pyridylmethyl)-(methyl)-amino-carbonyl-valine(p-nitrophenyl)ester 12-1) Preparation of 2-(methylaminomethyl) pyridine Methylamine gas was bubbled through the benzene solution(60 ml) of 10.7 g(100 mmol) of 2-pyridinecarboxaldehyde for 2 hours. Benzene was distilled off under a reduced pressure and the residue was taken up in 40 ml of ethanol. To the resulting solution was added 5.7 g of $NaBH_4$ in three portions and the resulting mixture was stirred at room temperature for 8 hours. To the reaction mixture was added 0.5N hydrochloric acid with care not to allow the pH below 6. 300 ml of dichloromethane was added thereto and the resulting solution was washed three times with 1M $NaHCO_3$ solution of pH 10. The organic layer was concentrated under a reduced pressure to give 10.4 g of the title compound(yield: 85%).

$^1H$ NMR($CDCl_3$) δ 2.1(s, 1H), 2.5(s, 3H), 3.9(s, 2H), 7.1(t, 1H), 7.3(d, 1H), 7.6(t, 1H), 8.5(d, 1H)

12-2) Preparation of N,N-(2-pyridyl methyl)-(methyl)-amino-carbonyl-valine ethylester A solution of 9.0 g(50 mmol) of L-valine ethylester hydrochloride dissolved in 300 ml of 20% phosgene toluene solution was heated at 100° C. for 2 hours. The solution was cooled to room temperature and distilled under a reduced pressure. The residue was dissolved in 150 ml of dichloromethane, and the resulting solution was cooled to 0° C. A dichloromethane solution(50 ml) of 5.86 g(48 mmol) of the product obtained in the Preparation Example 12-1) was added slowly to the resulting mixture over 10 minutes. The reaction mixture was warmed to room temperature and stirred for 3 hours. The organic layer was washed with brine, dried over anhydrous $MgSO_4$ and concentrated under a reduced pressure to give 12.9 g of the title compound(yield: 92%)

$^1H$ NMR($CDCl_3$) δ 0.9(m, 6H), 1.2(t, 3H), 2.2(m, 1H), 3.0(s, 3H), 4.1(m, 2H), 4.4(m, 1H), 4.5(s, 2H), 6.0(b, 1H), 7.2(m, 2H), 7.7(t, 1H), 8.5(d, 1H)

12-3) Preparation of N,N-(2-pyridyl methyl)-(methyl)-amino-carbonyl-valine

To a methanolic solution(100 ml) of 8.8 g(30 mmol) of the product obtained in Preparation Example 12-2) was added 2.5 g(60 mmol) of lithium hydroxide(LiOH $H_2O$) and the whole mixture was stirred at room temperature for 10 hours. Methyl alcohol was distilled off under a reduced pressure and 7.7 g of the title compound was isolated by using Dowex 50W-X8 cation exchange resin(5×20 cm) (yield: 97%).

$^1H$ NMR($CDCl_3$) δ 0.9(m, 6H), 2.1(m, 1H), 3.1(s, 3H), 4.0(d, 1H), 5.0(m, 2H), 7.9(m, 2H), 8.5(t, 1H), 8.7(d, 1H)

12-4) Preparation of N,N-(2-pyridylmethyl)-(methyl)-amino-carbonyl-valine(p-nitrophenyl) ester To a solution of 265 mg of the product obtained in Preparation Example 12-3) in 5 ml of DMF was added successively 206 mg(1 mmol) of dicyclohexylcarbodiimide and 167 mg(1.2 mmol) of 4-nitrophenol at 0° C. The resulting solution was warmed to room temperature over 30 minutes and then stirred for 2 hours. The solution was concentrated under a reduced pressure and filtered using ethyl acetate. The filtrate was concentrated under a reduced pressure and used in the next reaction at once.

PREPARATION EXAMPLE 13

Preparation of N-(2-pyridyl methoxy carbonyl) valine

The same procedures as described in Preparation Example 12-2) and 12-3) were repeated using 2-pyrindinecarbinol in place of 2-(methylaminomethyl)pyridine to give 7 g of the title compound(yield: 92%).

$^1$H NMR(CDCl$_3$) δ 0.9(m, 6H), 2.1(m, 1H), 3.9(d, 1H), 5.1(s, 1H), 7.3(t, 1H), 7.5(d, 1H), 7.8(t, 1H), 8.4(d, 1H)

PREPARATION EXAMPLE 14

Preparation of 2-L-(t-butoxycarbonyl) amino-1,6-diphenylhex-3-cis-ene 14-1) Preparation of N-t-butoxycarbonyl-L-phenylalanine methyl ester To a solution of 8.8 g(0.0344 mol) of N-t-butoxycarbonylphenylalanine in 50 ml of dichloromethane were successively added 5.25 ml of triethylamine solution, and 3 ml of chloromethylformate at 0° C. 50 mg of 4-dimethylaminopyridine was added to catalyze the reaction. After the reaction was completed the reaction mixture was extracted with dichloromethane and distilled under a reduced pressure to give the title compound quantitatively.

$^1$H NMR(CDCl$_3$) δ 1.4(9H, s), 3.1(2H, m), 3.7(3H, s), 4.6(1H, m), 5.0(1H, d), 7.1–7.3(5H, m)

14-2) Preparation of N-t-butoxycarbonyl-L-phenylalanal

N-t-butoxycarbonyl-L-phenylalanine methyl ester(1.3 g) obtained in Preparation Example 14-1) was dissolved in 20 ml of dry toluene and the solution was cooled to −78° C. with dry ice-acetone. To the solution was added slowly 10 ml of 1M solution of diisobutylaluminium hydride in hexane over 2 hours under nitrogen atmosphere. After stirred for 50 minutes, excess of diisobutylaluminium hydride was destroyed by the addition of 5 ml of methanol at −78° C. The reaction mixture was warmed to room temperature, extracted with ethyl acetate, dried over anhydrous MgSO$_4$ and concentrated to give 1.1 g of the title compound (yield: 95%). The product was used in the next reaction without further purification.

$^1$H NMR(CDCl$_3$) δ 1.4(9H, s), 3.1(2H, m), 4.4(1H, m), 5.2(1H, d), 7.1–7.3(5H, m), 9.8(1H, s)

14-3) Preparation of 3-(phenylpropyl)triphenylphosphine bromide 19.9 g(0.1 mol) of 1-bromo-3-phenylpropane and 26.2 g (0.1 mol) of triphenylphosphine were dissolved in 300 ml of dry toluene and the mixture was heated at reflux overnight. The reaction mixture was cooled to room temperature and filtered to obtain the white solid. This solid was washed with 100 ml of diethylether and dried over P$_2$O$_5$ to give 28.1 g of the title compound(yield: 60%).

$^1$H NMR(CDCl$_3$) δ 1.92(2H, m), 3.03(2H, m), 3.85(2H, br), 7.12–7.29(5H, m), 7.60–7.84(15H, m)

14-4) Preparation of 2-L-(t-butoxycarbonyl)amino-1,6-diphenylhex-3-cis-ene

To a solution of 18.5 mg(0.04 mmol) of phosphine salt obtained in Preparation Example 14-3) in 2 ml of 1,4-dioxane was added 12.2 mg(0.08 mmol) of powdered K$_2$CO$_3$ and the mixture was stirred for 30 minutes. To the mixture was added 10.0 mg(0.04 mmol) of the compound obtained in Preparation Example 14-2) and the mixture was stirred at 90° C.–100° C. for further 30 minutes. The resulting solution was cooled and filtered to remove solid. The filtrate was diluted with 20 ml of diethyl ether and the resulting solution was washed twice with each 10 ml of distilled water. The resulting solution was dried over anhydrous MgSO$_4$, and concentrated under a reduced pressure. The residue was purified by column chromatography using hexane:ethyl acetate as an eluent to give 9.3 mg of the title compound(yield: 66%).

$^1$H NMR(CDCl$_3$) δ 1.39(9H, br), 2.15–2.08(6H, m), 4.30–4.62 (2H, br), 5.17(1H, t), 5.42(1H, m), 7.05–7.31 (10H, m)

Mass(FAB, m/e) 352(M+1)

PREPARATION EXAMPLE 15

Preparation of 2-L-(N-benzyloxycarbonyl-L-asparaginyl)amino-1,6-diphenylhex-3-cis-ene 15-1) Preparation of 2-L-amino-1,6-diphenylhex-3-ene trifluoroacetate 120 mg of the compound obtained in Preparation Example 14-4) was dissolved in 3 ml of dichloromethane, and 2 ml of trifluoroacetic acid was added thereto. The resulting solution was stirred at room temperature for 30 minutes and concentrated under a reduced pressure to produce the title compound quantitatively.

$^1$H NMR(CDCl$_3$) δ 2.7(2H, m), 3.0(2H, t), 3.2–3.5(2H, m), 4.6(1H, br), 5.9(1H, m), 6.3(1H, m), 7.4–8.0 (10H, m), 10.5(3H, br)

15-2) Preparation of 2-L-(N-benyloxycarbonyl-L-asparaginyl)amino-1,6-diphenylhex-3-cis-ene 17 mg(0.067 mmol) of N-benzyloxycarbonyl-L-asparagine, 15 mg of 3-ethyl-3'-(dimethylamino) propylcarbodiimide and 10 mg of N-hydroxybenzotriazole were dissolved in 5 ml of dry dimethylformamide and the mixture was stirred for 30 minutes. To the mixture were added 18 mg(0.05 mmol) of the compound obtained in Preparation Example 15-1) and 10 μl of N-methyl morpholin, and stirring was continued at room temperature for 24 hours. The reaction mixture was distilled under a reduced pressure to remove dimethylformamide and the residue was dissolved in 30 ml of ethyl acetate. The resulting solution was washed each three times respectively with 30 ml of 1N HCl and 30 ml of saturated NaHCO$_3$ solution, and then dried over anhydrous MgSO$_4$. The solvent was removed and the residue was purified by column chromatography using ethyl acetate:hexane (2:5) as an eluent to give 14.5 mg of the title compound (yield: 60%)

$^1$H NMR(CDCl$_3$) δ 0.8(6H, m), 2.0(1H, m), 2.2–2.9(6H, m), 3.9(1H, m), 4.9(1H, m), 5.1(2H, m), 5.2(1H, m), 5.3(1H, d), 5.5(1H, m), 5.8(1H, d), 7.1–7.4 (15H, m)

PREPARATION EXAMPLE 16

Preparation of 2-L-(N-benzyloxycarbonyl-L-valinyl) amino-1,6-diphenyl hex-3-cis-ene The same procedures as described in Preparation Example 15-2) were repeated using N-benzyloxycarbonyl-L-valine in place of N-benzyloxycarbonyl-L-asparagine to give the title compound(yield: 70%).

$^1$H NMR(CDCl$_3$) δ 0.8(6H, m), 2.0(1H, m), 2.2–2.9(6H, m), 3.9(1H, m), 4.9(1H, m), 5.1(2H, m), 5.2(1H, m), 5.3(1H, d), 5.5(1H, m), 5.8(1H, d), 7.1–7.4 (15H, m)

PREPARATION EXAMPLE 17

Preparation of 2-L-(N-benzyloxycarbonyl-L-isoleucinyl)amino-1,6-diphenylhex-3-cis-ene The same procedures as described in Preparation Example 15-2) were repeated using N-benzyloxycarbonyl-L-isoleucine in place of N-benzyloxycarbonyl-L-asparagine to give the title compound(yield: 70%).

$^1$H NMR(CDCl$_3$) δ 0.8(6H, m), 1.0–1.5(2H, m), 1.8(1H, m), 2.2–2.8(6H, m), 3.9(1H, m), 4.9(1H, m), 5.1 (2H, s), 5.2(2H, m), 5.5(1H, m), 5.8(1H, d), 7.1–7.4(15H, m)

PREPARATION EXAMPLE 18

Preparation of 2-L-(N-benzyloxycarbonyl-L-glutaminyl)amino-1,6-diphenylhex-3-cis-ene The same procedures as described in Preparation Example 15-2) were repeated using N-benzyloxycarbonyl-L-glutamine in place of N-benzyloxycarbonyl-L-asparagine to give the title compound(yield: 60%).

$^1$H NMR(CDCl$_3$) δ 0.8(6H, m), 2.0(1H, m), 2.2–2.9(8H, m), 3.9(1H, m), 5.0(1H, m), 5.1(2H, m), 5.2 (1H, m), 5.3(1H, d), 5.5(1H, m), 5.8(1H, d), 7.1–7.4(15H, m)

PREPARATION EXAMPLE 19

Preparation of 2-L-(benzyloxycarbonyl)amino-1,6-diphenylhex-3-ene 19-1) Preparation of N-benzyloxycarbonyl-L-phenylalanine methyl ester The same procedures as described in Preparation Example 14-1) were repeated using N-benzyloxycarbonyl phenylalanine in place of N-t-butoxycarbonyl phenylalanine to give the title compound quantitatively.

19-2) Preparation of N-benzyloxycarbonyl-L-phenylalanal 6.0 g(0.019 mol) of the compound obtained in Preparation Example 19-1) was dissolved in 100 ml of dry toluene and the solution was cooled to −50° C. with dry ice-acetone. 22 ml of 1.76M diisobutylaluminium hydride solution in hexane was added slowly to the above solution over 30 minutes with vigorous stirring under nitrogen atmosphere. The resulting solution was stirred for further 20 minutes and excess of diisobutylaluminium hydride was destroyed by adding 100 ml of 2N HCl thereto. The reaction mixture was warmed to 0° C. and then extracted twice with each 60 ml of ethyl acetate. Combined organic layer was washed with 200 ml of saturated NaCl solution, dried over anhydrous $MgSO_4$ and distilled under a reduced pressure to give 3.8 g of desired compound. The resulting compound was used in the next reaction without further purification.

$^1$H NMR($CDCl_3$) δ 3.05–3.20(2H, d), 4.52(1H, q), 5.10 (2H, s), 5.31(1H, br), 7.10–7.43(10H, m), 9.63(1H, s)

Mass(FAB, m/e) 284(M+1)

19-3) Preparation of 2-L-(benzyloxycarbonyl)amino-1,6-diphenylhex-3-ene

The same reaction procedures as described in Preparation Example 14-4) were repeated using the compound obtained in Preparation Example 19-2) to give the title compound as a mixture(9:1) of cis-and trans-isomers(yield: 60%).

The mixture was purified by column chromatography using hexane:ethyl acetate(6:1) as an eluent.

PREPARATION EXAMPLE 20

Preparation of N-morpholinecarbonyl-L-alanine 4 g(50 mmol) of L-alanine and 2 g(50 mmol) of NaOH were added to 30 ml of distilled water. The mixture was cooled to 0° C. and then stirred vigorously. To the mixture was added slowly a solution of 7.1 g(50 mmol) of morpholinecarbonyl-chloride in 30 ml of tetrahydrofuran, while adjusting the whole mixture to pH 8.5–pH 9.5 with the addition of 0.05N NaOH. After the reaction was completed, the reaction mixture was acidified to pH 2 with 6N HCl. The reaction mixture was extracted with a mixed solvent of ethyl acetate and THF(1:1) (30 ml×3) and the organic layer was concentrated under a reduced pressure to give 4 g of the title compound(yield: 40%).

$^1$H NMR($D_2O$) δ 1.3(3H, d), 3.2(4H, br), 3.6(4H, br), 4.0(1H, q)

PREPARATION EXAMPLE 21

Preparation of 5-L-amino-7-methyl-1-phenyl-oct-3-cis-ene trifluoroacetate 21-1) Preparation of N-t-butoxycarbonyl-L-leucine methyl ester The same procedures as described in Preparation Example 14-1) were repeated using N-t-butoxycarbonylleucine in place of N-t-butoxycarbonylphenylalanine to give the title compound.

21-2) Preparation of N-t-butoxycarbonyl-L-leucinal

The same procedures as described in Preparation Example 14-2) were repeated using N-t-butoxycarbonyl-L-leucine methyl ester obtained in Preparation Example 21-1) in place of N-t-butoxycarbonyl-L-phenylalanin methyl ester to give the title compound.

21-3) Preparation of 5-L-[N-(t-butoxycarbonyl)]amino-7-methyl-1-phenyl-oct-3-cis-ene 215 mg(1 mmol) of N-t-butoxycarbonyl-L-leucinal obtained in Preparation Example 21-2), 262 mg(1 mmol) of 3-(phenylpropyl) triphenylphosphine bromide obtained in Preparation Example 14-3) and 200 mg of $K_2CO_3$ were dissolved in 10 ml of 1,4-dioxane and the mixture was refluxed for 4 hours. After the reaction was completed, precipitates were filtered off and the filtrate was distilled under a reduced pressure to remove 1,4-dioxane. The residue was taken up in 100 ml of diethyl ether, and the resulting solution was dried over anhydrous $MgSO_4$, distilled under a reduced pressure and purified by column chromatography using ethyl acetate:hexane(1:8) as an eluent to give 300 mg of the title compound(yield: 95%).

$^1$H NMR($CDCl_3$) δ 0.9(6H, 2d), 1.1–1.7(3H, m), 1.4(9H, m), 2.3–2.8(4H, m), 4.2–4.5(2H, m), 5.2(1H, m), 5.5(1H, m), 7.1–7.3(5H, m)

Mass(FAB, m/e) 318(M+1)

21-4) Preparation of 5-L-amino-7-methyl-1-phenyl-oct-3-cis-ene trifluoroacetate 42 mg(0.13 mmol) of the compound obtained in Preparation Example 21-3) was dissolved in 1 ml of dichloromethane and 1 ml of trifluoroacetic acid was added thereto. The mixture was stirred at room temperature for 30 minutes and concentrated under a reduced pressure to give the title compound quantitatively.

$^1$H NMR($CDCl_3$) δ 0.8(6H, 2d), 1.3–1.5(3H, m), 2.4(2H, m), 2.7(2H, m), 3.9(1H, br), 5.3(1H, m), 5.8 (1H, m), 7.0–7.3(5H, m), 10.5(3H, br)

PREPARATION EXAMPLE 22

Preparation of 2-L-(benzyloxycarbonylamino)-7-methyl-1-phenyl-oct-3-cis-ene

To a solution of 2.49 g(10 mmol) of L-phenylalanal and 4.27 g(10 mmol) of 4-methyl-1-pentyltriphenylphosphoniumbromide dissolved in 50 ml of 1,4-dioxane was added 2.76 g (20 mmol) of powdered $K_2CO_3$, and the reaction mixture was stirred at reflux temperature of the reaction solvent for 5 hours. The reaction mixture was cooled to 0° C., and filtered to remove solid. The filtrate was diluted with 30 ml of diethyl ether, washed twice with each 10 ml of distilled water, dried over anhydrous $MgSO_4$ and distilled under a reduced pressure. The residue was purified by column chromatography using hexane:ethyl acetate (10:1) as an eluent to give 2.02 g of the title compound (yield: 60%).

$^1$H NMR($CD_3OD$) δ 0.8(6H, d), 1.1–1.5(5H, m), 1.8(1H, m), 2.8(2H, m), 5.0(2H, s), 5.05–5.3(2H, m), 7.0–7.4(10H, m)

PREPARATION EXAMPLE 23

Preparation of N-morpholinesulfonyl chloride

A mixture of 16 g of conc. hydrochloric acid, 16 g of water and 14.2 g of morpholine was cooled to 5° C. and 80 ml of dichloromethane was added thereto. 315 g of 4% NaOCl was added at 5° C. over 60 minutes and the mixture was stirred at room temperature for 50 minutes. The dichloromethane layer was separated, dried over MgSO$_4$ and cooled to −70° C. 24 g of SO$_2$ and 100 ml of dichloromethane were further added thereto. 3 ml of chlorine gas was condensed into the resulting mixture and the mixture was stirred for 24 hours, while warmed gradually to room temperature. The mixture was washed with 0.25M phosphate buffer, pH 7.0 until the washings are neutral. The dichloromethane layer was dried over anhydrous MgSO$_4$ and distilled under a reduced pressure to give the title compound (yield: 60%).

$^1$H NMR(CDCl$_3$) δ 1.2–1.7(5H, m, d), 2.4–3.2(12H, m), 3.7 (4H, br), 3.9(2H, m), 4.7(1H, m), 6.8(1H, br), 6.9(1H, br), 7.05–7.4(10H, m), 7.5(1H, d), 7.7–7.8(1H, dd), 8.3–8.5 (1H, dd)

Mass(FAB, m/e) 602(M+1)

PREPARATION EXAMPLE 24

Preparation of 4S-1,4-bis[(N-benzyloxycarbonyl) amino]-5-phenyl-(2,3)-(Z)-pentene 24-1) Preparation of N-[(2-triphenyl phosphine)ethyl] phthalimide bromide 2.54 g(10 mmol) of N-(2-bromoethyl)phthalimide and 2 equivalents of triphenyl phosphine was stirred at 150° C. for 16 hours without solvent and then crystallized from ethanol and ether to give 4.54 g of the title compound(yield: 88%).

$^1$H NMR(CDCl$_3$) 4.32(m, 2H), 4.54(m, 2H), 7.51–7.71 (m, 15H), 7.81–7.93(m, 4H)

24-2) Preparation of 4S-[(N$^1$-phthaloyl)amino]-[(N$^4$-benzyloxycarbonyl)amino]-5-phenyl-(2,3)-pentene 0.568 g(1.1 mmol) of the product obtained in Preparation Example 24-1) and 0.283 g(1 mmol) of N-benzyloxycarbonyl-L-phenylalaninal were dissolved in a mixture of dioxane(30 ml) and dimethyl sulfoxide(10 ml) and the reaction mixture was stirred at 70° C. for 5 hours. The resulting solution was distilled under a reduced pressure to remove dioxane, diluted with 80 ml of ethyl acetate and washed with saturated NaCl solution. The organic layer was separated and dried over anhydrous MgSO$_4$. The residue was chromatographed over silica gel with hexane:ethyl acetate(7:3) as an eluent to give 0.374 g of the product as a 8:1 mixture of cis- and trans-isomers (yield: 85%).

$^1$H NMR(CDCl$_3$) 2.78–2.99(m, 2H), 4.26(m, 2H), 4.59 (bs, 1H), 4.85(m, 1H), 5.10(S, 2H), 5.44–5.58(m, 2H), 7.15–7.32(m, 10H), 7.72–7.95(m, 4H)

24-3) Preparation of 4S-[(N$^4$-benzyloxycarbonyl)amino]-1-amino-5-phenyl-(2,3)-pentene 0.44 g(1 mmol) of the product obtained in Preparation Example 24-2) and 3 equivalents of hydrazine were dissolved in 20 ml of ethanol and the reaction mixture was refluxed for 3 hours. The resulting solid was removed by filtration and the filtrate was distilled under a reduced pressure to remove organic solvent. The residue was dissolved in 50 ml of ethyl acetate, and the resulting solution was washed with 0.2N NaOH solution and dried over anhydrous Na$_2$SO$_4$ to give 0.298 g of the title compound (yield: 96%).

$^1$H NMR(CDCl$_3$) 2.65–3.23(m, 4H), 4.64(m, 1H), 5.11(S, 2H), 5.15–5.54(m, 2H), 7.09–7.43(m, 10H)

24-4) Preparation of 4S-1,4-bis-[(N-benzyloxycarbonyl) amino]-5-phenyl-(2,3)-(Z)-pentene 0.31 g(1 mmol) of the product obtained in Preparation Example 24-3) and 3 equivalents of triethylamine were dissolved in 20 ml of dry dichloromethane and 1.1 equivalent of N-benzyloxycarbonyl chloride was added slowly at 0° C. The reaction mixture was stirred at room temperature for 3 hours. The organic solvent was removed by distillation under a reduced pressure and 30 ml of ethyl acetate was added to the residue. The resulting solution was washed with 1N hydrochloric acid and dried over anhydrous MgSO$_4$. The residue was purified by column chromatography using hexane:ethyl acetate(8:2) as an eluent to give the title compound having olefinic linkage between 2-and 3-position, i.e., 0.373 g(yield: 96%) of cis-isomer and 47 mg(yield: 96%) of trans-isomer.

$^1$H NMR(CDCl$_3$) cis-olefinic isomer 2.71(m, 1H), 2.95 (m, 1H), 3.48–3.79(m, 2H), 4.65 (m, 1H), 4.80(m, 2H), 5.11(s, 4H), 5.33(t, 1H), 5.52(m, 1H), 7.13–7.42(m, 15H)

$^1$H NMR(CDCl$_3$) trans-olefinic isomer 2.81(m, 2H), 3.77 (m, 2H), 4.45(m, 1H), 4.71 (bs, 2H), 5.11(d, 4H), 5.55(m, 2H), 7.09–7.48 (m, 15H)

PREPARATION EXAMPLE 25

Preparation of 4S-1,4-bis[(N-benzyloxycarbonyl) amino]-5-phenyl-(2S,3R)-(Z)-epoxy pentane 0.46 g(1 mmol) of cis-olefin compound obtained in Preparation Example 24-4) and 3 equivalents of metachloroperoxybenzoic acid were dissolved in 30 ml of dry dichloromethane and the reaction mixture was stirred at room temperature for 16 hours. The reaction mixture was washed successively with 50 ml of 10% Na$_2$S$_2$O$_3$ solution and 50 ml of saturated NaHCO$_3$ solution, and dried over anhydrous MgSO$_4$. The residue was purified by column chromatography using hexane:ethyl acetate (7:3) as an eluent to give 0.40 g of the title compound(yield: 87%).

$^1$H NMR(CDCl$_3$) 2.75–3.14(m, 6H), 3.71(m, 1H), 4.42 (bs, 1H), 5.10(d, 4H), 5.15(bs, 1H), 7.15–7.41(m, 15H)

PREPARATION EXAMPLE 26

Preparation of 4S-[N$^1$-[(N-benzyloxycarbonyl-L-asparaginyl)amino]]-[N$^4$-(t-butoxycarbonyl)amino]-5-phenyl-2,3-(Z)-pentene 552 mg(1 mmol) of compound 30 in Table 5 and 1.2 equivalent of N-benzyloxycarbonyl-L-asparagine were dissolved in 1.5 ml of dry dimethylformamide and the reaction mixture was stirred at room temperature for 16 hours. The resulting solution was distilled under a reduced pressure to remove organic solvent and 50 ml of ethyl acetate was added thereto. The resulting solution was washed with 50 ml of saturated NaHCO$_3$ solution and the organic layer was dried over anhydrous MgSO$_4$. The residue was purified by column chromatography using dichloromethane:methanol(9:1) as an eluent to give 860 mg of the title compound (yield: 82%).

$^1$H NMR(CDCl$_3$) 1.39(s, 9H), 2.52–2.71(m, 2H), 2.89(m, 2H), 3.68(m, 2H), 4.45–4.64(m, 2H), 5.12(s, 2H), 5.28–5.47 (m, 2H), 5.85(bs, 1H), 6.19–6.24 (m, 2H), 6.74(bs, 2H), 7.15–7.48(m, 10H)

FABMS 525(M+1)

PREPARATION EXAMPLE 27

Preparation of 4S-[N$^1$-[(N-benzyloxycarbonyl-L-asparaginyl)amino]]-[N$^4$-[(N-benzyloxycarbonyl-L-valinyl) amino]]-5-phenyl-2,3-(Z)-pentene 786 mg(1.5 mmol) of the product obtained in Preparation Example 26 was dissolved in a mixture of dichloromethane (10 ml) and trifluoroacetic acid(5 ml) and the reaction mixture was stirred at room temperature for 2 hours. The solution was distilled under a reduced pressure to remove organic solvent and the residue was dissolved in 10 ml of dry dimethylformamide together with 1.2 equivalent of N-benzyloxycarbonyl-L-valine, 1.5 equivalent of EDC, 1.5 equivalent of HOBT and 3 equivalent of triethylamine. The whole mixture was stirred at room temperature for 16 hours. The mixture was concentrated under a reduced pressure to remove organic solvent and 50 ml of ethyl acetate was added to the residue. The resulting solution was washed with saturated NaHCO$_3$ solution and the organic layer was dried over anhydrous MgSO$_4$. The residue was purified by column chromatography using dichloromethane:methanol(15:1) as an eluent to give 572 mg of the title compound(yield: 58%).

$^1$H NMR(DMSO) 0.79–1.03(m, 6H), 2.03(m, 1H), 2.60 (m, 2H), 2.97(m, 2H), 3.72(m, 2H), 4.28(m, 1H), 4.46 (m, 1H), 4.91(m, 1H), 5.15(s, 4H), 5.45(m, 2H), 6.92(bs, 2H), 7.15–7.55(m, 15H), 7.92–8.20 (m, 2H), 5.75(bs, 2H)

FABMS 658(M+1)

PREPARATION EXAMPLE 28

Preparation of 4S-[N$^1$-(t-butoxycarbonyl)amino]-[(N$^4$-benzyloxycarbonyl)amino]-5-phenyl-2,3-(Z)-pentene To a solution of 310 mg(1 mmol) of 4S-[(N$^4$-benzyloxycarbonyl)amino]-1-amino-5-phenyl-(2,3)-pentene obtained in Preparation Example 24-3) in 20 ml of dry dichloromethane was added 1.2 equivalent of t-butoxycarbonyl anhydride and the reaction mixture was stirred at room temperature for 16 hours. The organic solvent was removed and the residue was purified by column chromatography using hexane:ethyl acetate(8:2) as an eluent to give 377 mg of the title compound(yield: 92%).

$^1$H NMR(CDCl$_3$) 1.41(s, 9H), 2.62(m, 1H), 2.95(m, 1H), 3.42–3.71 (m, 2H), 4.48–4.70(m, 2H), 4.89(bs, 1H), 5.05 (s, 2H), 5.29(t, 1H), 5.49(m, 1H), 7.10–7.35 (m, 10H)

PREPARATION EXAMPLE 29

Preparation of 4S-[N$^1$-(t-butoxycarbonyl)amino]-[N$^4$-(benzyloxycarbonyl)amino]-5-phenyl-(2S,3R)-(Z)-epoxypentane To a solution of 328 mg(0.8 mmol) of the product obtained in Preparation Example 28 dissolved in 20 ml of dry dichloromethane was added 3 equivalents of metachloroperoxybenzoic acid and the reaction mixture was stirred at room temperature for 16 hours. The resulting solution was washed successively with 30 ml of 10% Na$_2$S$_2$O$_3$ solution and 30 ml of saturated NaHCO$_3$ solution, and purified by column chromatography using hexane:ethyl acetate(7:3) as an eluent to give 306 mg of the title compound(yield: 92%).

$^1$H NMR(CDCl$_3$) 1.41(s, 9H), 2.67–3.18(m, 6H), 3.63(m, 1H), 4.48 (bs, 1H), 4.85(d, 1H), 5.05(s, 2H), 7.13–7.42 (m, 10H)

PREPARATION EXAMPLES 30 TO 42

The same procedures as described in Preparation Example 24 or 25 were repeated using L-phenylalanine as a starting material to give the compounds listed in Table 5 below. (N-benzyloxycarbonyl)-L-cyclohexyl phenylalaninal was prepared according to a method described by Boger et al. in J.Med. Chem. 28, 1779(1985).

EXAMPLE 1

Preparation of N-[5-L-[[N-(2-quinolinecarbonyl)-L-asparaginyl]amino]-epoxy-6-phenyl-hexanoyl]-L-isoleucine methyl ester(compound No. 2)

212 mg(0.44 mmol) of the compound obtained in Preparation Example 8-2) was dissolved in 15 ml of dry methanol and 40 mg of 10% Pd/C was added thereto. The reaction mixture was stirred at room temperature under 1 atmosphere of hydrogen for 5 hours to remove benzyloxycarbonyl group. The resulting solution was filtered through Celite and the organic solvent was concentrated in vacuo. The residue was dissolved in 3 ml of dry dimethyl-formamide together with 1 equivalent of N-(2-quinoline-carbonyl)-L-asparagine, 1.2 equivalent of EDC, 1.2 equivalent of HOBT and 1.5 equivalent of triethylamine. The resulting mixture was stirred at room temperature for 20 hours. The resulting solution was distilled under a reduced pressure to remove dimethylformamide and the residue was diluted with 30 ml of dichloromethane. The resulting solution was washed with saturated NaHCO$_3$ solution and the organic layer was dried over anhydrous MgSO$_4$. The residue was purified by column chromatography using ethyl acetate as an eluent to give 190 mg of the title compound(yield: 70%).

$^1$H NMR(CDCl$_3$) δ 0.9(m, 6H), 1.2–1.5(m, 2H), 1.9(m, 1H), 2.3–3.4(m, 6H), 3.7(s, 3H), 4.2–4.6(m, 2H), 5.05(m, 1H), 5.8–6.6(s, s, 2H), 6.9–7.5(m, 6H), 7.6–8.4(m, 6H), 8.9–9.4(d, 1H)

Mass(FAB, m/e) 618(M+1)

EXAMPLE 2

Preparation of N-[5-L-[[N-(2-quinolinecarbonyl)-L-asparaginyl]amino]-epoxy-6-phenyl-hexanoyl]-L-isoleucine methyl ester(compound No. 2)

2-1) Preparation of N-[5-L-(N-benzyloxycarbonylamino)-(4R,3S)-epoxy-6-phenyl-hexanoyl]-L-isoleucine methyl ester Each 1 equivalent of the compound obtained in Preparation Example 9-4) and L-isoleucine-methyl ester were dissolved in dimethylformamide. The same procedures as described in Example 1 were repeated using the above mixture, 1.2 equivalent of EDC, 1.2 equivalent of HOBT and 1.5 equivalent of triethylamine in place of those reactants used in Example 1 to give the title compound. NMR and FABMS data of the title compound are the same as those of the compound prepared in Preparation Example 8-2).

2-2) Preparation of N-[5-L-[[N-(2-quinolinecarbonyl)-L-asparaginyl]amino]-epoxy-6-phenyl-hexanoyl]-L-isoleucine methyl ester(2)

The same procedures as described in Example 1 were repeated to obtain the title compound. NMR and FABMS data of the title compound are the same as those of the title compound prepared in Example 1.

EXAMPLES 3 TO 25

The same procedures as described in Example 1 or Example 2 were repeated to obtain the compound 1 and 3 to 24 listed in Table 1, respectively, and their NMR and FABMS data are shown in Table 6 below. (N-benzyloxycarbonyl)-L-cyclohexylphenylalaninal was prepared according to a method described by Boger et al. in J. Med. Chem. 28, 1779–1790(1985), and (2R)-hydroxy-(1S)-amino-indane was prepared according to a method described by Thompson et al. in J. Med. Chem. 35, 1685–1701(1992).

EXAMPLE 26

Preparation of N-{5-L-[[N-(2-quinolinecarbonyl)-L-asparaginyl]amino]-(4R,3S)-epoxy-6-phenylhexanoyl}-L-isoleucinyl-(N-methoxy)-amine (28)

350 mg(7 mmol) of the product obtained in Preparation Example 10-3) was dissolved in 30 ml of methanol and benzyloxycarbonyl group was removed therefrom according to a method of Preparation Example 10-2). After concentration, the residue was mixed with a solution of 200 mg(7 mmol) of L-(N-2-quinolinecarbonyl)asparginyl carbonylic acid, 161 mg(8.4 mmol) of EDC hydrochloride, 122 mg(9.1 mmol) of 1-hydroxy benzotriazol hydrate and 106 mg(10.5 mmol) of triethylamine dissolved in 30 ml of dry dimethylformamide and the mixture was stirred at room temperature for 5 hours. The resulting solution was concentrated under a reduced pressure and the residue was taken up in 50 ml of dichloromethane, which was washed with 50 ml of $NaHCO_3$ solution. The organic layer was dried over anhydrous $MgSO_4$ and concentrated in vacuo. The residue was purified by column chromatography using methylene chloride:methanol(15:1) as an eluent to give 150 mg of the title compound(yield: 33.8%).

$^1$H NMR(CDCl$_3$) δ 0.9(m, 6H), 1.0–2.0(m, 3H), 2.2–3.5 (m, 8H), 3.8(s, 3H), 4.0(m, 1H), 4.4(m, 1H), 5.0(m, 1H), 5.2(d, 1H, NH), 5.3–6.4(m, 2H, NH), 7.2–7.4 (m, 5H), 7.6–8.3(m, 6H), 8.8–9.4(d, 1H, NH)

Mass(FAB, m/e) 633(M+1)

EXAMPLE 27

Preparation of N-{5-L-[[N-(2-quinolinecarbonyl)-L-asparaginyl]amino]-(4R,3S)-epoxy-6-phenylhexanoyl}-L-isoleucinyl-methylamide(25)

The same procedures as described in Example 26 were repeated using 300 mg(0.6 mmol) of the product obtained in Preparation Example 11-4) to give 80 mg of the title compound (yield: 14.4%).

$^1$H NMR(CDCl$_3$) δ 0.9(m, 6H), 1.0–2.0(m, 3H), 2.6–3.0 (m, 11H), 4.3(m, 2H), 5.0(m, 1H), 5.1(m, 1H, NH), 6.0–7.0 (m, 2H), 7.1–7.4(m, 5H), 7.6–8.3 (m, 6H), 8.8–9.4(d, 1H)

Mass(FAB, m/e) 617(M+1)

EXAMPLE 28

Preparation of N-{5-L-[[N-(2-quinolinecarbonyl)-L-asparaginyl]amino]-(4R,3S)-epoxy-6-phenylhexanoyl}-L-isoleucinyl amide(27)

200 mg(4.2 mmol) of [5-L-(N-benzyloxycarbonyl)amino-(4R,3S)-epoxy-6-phenyl-hexanoyl]-L-isoleucine amide was prepared from the product obtained in Preparation Example 11-1) by using the methods of Preparation Example 10-2) and 10-3). The same procedures as described in Example 26 were repeated using the above product to give 60 mg of the title compound(yield: 23.8%).

$^1$H NMR(CDCl$_3$) δ 0.9(m, 6H), 1.0–2.0(m, 3H), 2.2–3.5 (m, 8H), 4.6(m, 1H), 4.4(m, 1H), 5.0(m, 1H), 7.2–7.4 (m, 5H), 7.6–8.3(m, 6H)

Mass(FAB, m/e) 603(M+1)

EXAMPLE 29

Preparation of N-{N-L-[[N,N-(2-pyridylmethyl)-(methyl)-amino]carbonyl valinyl]amino-(4R,3S)-epoxy-6-phenyl-hexanoyl}-L-isoleucine methyl ester(35)

Benzyloxycarbonyl group was removed from the title compound of Preparation Example 2-1) in accordance with the method of Preparation Example 10-2) to obtain amine compound. 320 mg (0.9 mmol) of the resulting amine was dissolved in 8 ml of dichloromethane and the solution was subjected to coupling reaction with the product of Preparation Example 12-4) in accordance with the method described in Example 26. 390 mg of the title compound was obtained through column chromatography (yield: 72%).

$^1$H NMR(CDCl$_3$) δ 0.9(m, 12H), 1.2(m, 1H), 1.4(m, 1H), 1.8 (m, 1H), 2.0(m, 1H), 2.2(m, 2H), 2.8–3.0 (m, 5H), 3.4–3.8(m, 6H), 4.4–4.7(m, 4H), 5.8 (d, 1H), 7.2t7.4(m, 7H), 7.7(m, 1H), 8.5(d, 1H)

Mass(FAB, m/e) 595(M+1)

EXAMPLE 30

N-{N-L-[[N-(2-pyridylmethoxycarbonyl)-L-valinyl)-amino]-(4R,3S)-epoxy-6-phenyl-hexanoyl}-L-isoleucine methyl ester(38)

The same procedures as described in Preparation Example 12-4) and Example 29 were repeated using the product of Preparation Example 13 to give the title compound(yield: 75%).

$^1$H NMR(CDCl$_3$) δ 0.9(m, 12H), 1.1–2.0(m, 17H), 2.1–2.3(m, 2H), 2.9(m, 1H), 3.4–3.8(m, 5H), 4.4–4.6(m, 2H), 5.0(s, 2H), 7.2–7.4(m, 7H), 7.8(t, 1H), 8.4 (d, 1H)

Mass(FAB, m/e) 583(M+1)

EXAMPLE 31

Preparation of N-{5-L-[[N,N-(2-pyridylmethyl)-(methyl)-amino]carbonyl valinyl]amino-(4R,3S)-epoxy-6-(cyclohexylmethyl)-hexanoyl}-L-isoleucine methyl ester(39)

The same procedures as described in Preparation Example 3, Example 2-1) and Example 29 were repeated using L-(N-benzyloxycarbonyl)-cyclohexyl alanal prepared according to a method described by Boger et al. in JMC 28, 1779–1790(1985) and L-(N-benzyloxycarbonyl)-isoleucine methyl ester to give the title compound.

$^1$H NMR(CDCl$_3$) δ 0.9(m, 12H), 1.1–2.0(m, 17H), 2.1–2.3(m, 2H), 2.9(m, 1H), 3.0(s, 3H), 3.4–3.8(m, 5H), 4.4–4.7(m, 4H), 7.2(m, 2H), 7.7(m, 1H), 8.5 (d, 1H)

Mass(FAB, m/e) 601(M+1)

EXAMPLES 32 TO 42

The same procedures as described in Examples 26 to 31 were repeated by using valine in place of isolencine or by introducing the functionalized amines such as dimethyl amine, morpholine or hydroxylamine into the carboxyl group in isoleucine and valine to obtain the compounds listed in Table 7.

TABLE 7

| Ex. No. (comp. No.) | compound | FABMS(M+1) | $^1$H NMR δ |
|---|---|---|---|
| 32 (26) | (structure with N(CH$_3$)$_2$ amide, sec-butyl, epoxide, benzyl, asparagine, quinoline-2-carboxamide) | 631 | (CDCl$_3$) 0.9(m, 6H), 1.0–2.0(m, 3H) 2.4–3.4(m, 14H), 4.4(m, 1H), 4.8(m, 1H), 5.1(m, 1H), 5.2(m, 1H), 5.9–6.4(m, 2H), 7.2–7.4(m, 5H), 7.6–8.4(m, 6H), 8.7–9.9(m, 1H) |
| 33 (29) | (structure with morpholine amide, sec-butyl, epoxide, benzyl, asparagine, quinoline-2-carboxamide) | 673 | (CD$_3$OD) 0.9(m, 6H), 1.0–2.0(m, 3H) 2.2–3.9(m, 16H), 4.0(m, 1H), 4.2(m, 1H), 5.0(m, 1H), 7.2–7.4(m, 5H), 7.6–8.3(m, 6H) |
| 34 (30) | (structure with NHCH$_3$ amide, isopropyl, epoxide, benzyl, asparagine, quinoline-2-carboxamide) | 603 | (CD$_3$OD) 0.8(m, 6H), 2.0–3.3(m, 12H) 4.3(m, 2H), 5.0(m, 1H), 7.2–7.5(m, 5H), 7.6–8.4(m, 6H) |

TABLE 7-continued

| Ex. No. (comp. No.) | compound | | $^1$H NMR δ |
|---|---|---|---|
| 35 (31) | [structure with quinoline, benzyl, epoxide, N,N-dimethyl amide] | 617 | (CD$_3$OD) 0.8(m, 6H), 2.0–3.4(m, 15H) 4.4(m, 1H), 4.8(m, 1H), 5.1(m, 1H), 7.2–7.5(m, 5H), 7.6–8.4(m, 6H) |
| 36 (32) | [structure with quinoline, benzyl, epoxide, primary amide] | 589 | (CD$_3$OD) 0.8(d, d, 6H), 2.1–3.5(m, 9H), 4.0(m, 1H) 4.1(m, 1H), 5.0(m, 1H), 7.2–7.4(m, 5H), 7.6–8.4(m, 6H) |
| 37 (33) | [structure with quinoline, benzyl, epoxide, morpholine amide] | 659 | (CDCl$_3$) 0.8(m, 6H), 2.1–3.9(m, 17H) 4.0–4.2(m, 2H), 5.0(m, 1H), 7.2–7.5(m, 5H), 7.7–8.4(m, 6H) |

TABLE 7-continued

| Ex. No. (comp. No.) | compound | Mass (FAB, M+1) | ¹H NMR δ |
|---|---|---|---|
| 38 (34) | | 619 | (CD₃OD) 0.8(m, 6H), 2.0–3.5(m, 9H) 3.9(s, 3H), 4.1–4.3(m, 2H), 5.0(m, 1H), 7.2–7.4(m, 5H) 7.6–8.4(m, 6H) |
| 39 (36) | | 580 | (CD₃OD) 0.9(m, 12H) 1.0–2.0(m, 4H) 2.2–3.5(m, 9H) 4.0(m, 1H), 4.5–4.7(m, 4H) 7.2–7.4(m, 7H), 7.6(m, 1H) 8.5(d, 1H) |
| 40 (37) | | 568 | (CD₃OD) 0.9(m, 12H) 1.0–2.0(m, 4H) 2.2–3.5(m, 6H) 4.0(m, 1H), 4.4–4.6(m, 2H) 5.0(s, 2H) 7.1–7.4(m, 7H) 7.8(t, 1H), 8.4(d, 1H) |

TABLE 7-continued

| Ex. No. (comp. No.) | compound | 1H NMR δ |
|---|---|---|
| 41 (40) | (quinoline-CO-NH-CH(CH2CONH2)-CO-NH-CH(CH2Ph)-[epoxide]-CH2-CO-NH-CH(CH(CH3)CH2CH3)-CO-NH-OH) | (CDCl$_3$) 0.8(m, 6H), 1.1(m, 1H) 1.4(m, 1H), 1.8(m, 1H), 2.2 (m, 1H), 2.7–3.3(m, 7H), 3.7(m, 1H), 4.5(m, 1H), 5.0(m, 1H), 5.1(m, 1H), 6.0–6.2(m, 2H), 7.1–8.3(m, 12H), 8.9(d, 1H), 9.9(s, 1H) |
| 42 (41) | (quinoline-CO-NH-CH(CH2CONH2)-CO-NH-CH(CH2Ph)-[epoxide]-CH2-CO-NH-CH(CH(CH3)2)-CO-NH-OH) | (CDCl$_3$) 0.8(m, 6H), 1.8(m, 1H) 2.3(m, 1H), 2.6–3.3(m, 7H), 3.8(m, 1H), 4.4(m, 1H), 5.0(m, 1H), 5.1(m, 1H), 6.0–6.2(m, 2H), 7.0–8.3(m, 12H), 8.9 (d, 1H), 10.0(s, 1H) |

EXAMPLE 43

Preparation of [[(5S)-[N-(2-quinolinecarbonyl)-L-asparaginyl]amino]-(4R,3S)-epoxy-6-phenyl-1-hexanoyl]-[(2S)-[1-phenyl-3-methyl]butyl]amide (42)

43-1) Preparation of [(5S)-[(N-benzyloxycarbonyl)amino]-3-(cis)-ene-6-phenyl-1-hexanoyl]-[(2S)-[1-phenyl-3-methyl]-butyl]amide To a stirred solution of 0.339 g(1 mmol) of the product obtained in Preparation Example 3-2) and each 1.5 equivalent of EDC, HOBT and triethylamine in 20 ml of dimethylformamide was added 0.163 g(1 mmol) of (S)-2-amino-3-methyl-1-phenylbutane at 0° C. The reaction mixture was stirred at room temperature for 12 hours and then distilled under a reduced pressure to remove the solvent. The residue was dissolved in 100 ml of ethyl acetate and the resulting solution was washed successively with 100 ml of 1N hydrochloric acid and 100 ml of saturated NaHCO₃ solution, dried over anhydrous MgSO₄ and concentrated under a reduced pressure. The residue was purified by column chromatography using ethyl acetate:hexane (1:1) as an eluent to give 0.38 g of the title compound(yield: 87.5%).

$^1$H NMR(CDCl₃) δ 0.85–1.01(m, 6H), 178(m, 1H), 2.42–2.25(m, 6H), 4.05(m, 1H), 4.58(m, 1H), 4.95(bs, 1H), 5.08 (m, 2H), 5.35(m, 1H), 5.58(m, 1H), 7.09–7.41 (m, 15H)

43-2) Preparation of [(5S)-[(N-benzyloxycarbonyl)amino]-(4R,3S)-epoxy-6-phenyl-1-hexanoyl]-(2S)-[[1-phenyl-3-methyl]-butyl]amide To a stirred solution of 360 mg(0.7 mmol) of the product obtained in Example 43-1) in 20 ml of dichloromethane was added 3 equivalents of metachloroperoxybenzoic acid and the reaction mixture was stirred at room temperature for 24 hours. To the mixture was added 20 ml of 10% Na₂S₂O₃ solution and stirring was continued for further 30 minutes. The organic layer was washed with saturated NaHCO₃ solution, and dried over anhydrous MgSO₄, and concentrated in vacuo. As a result, 0.30 g of the title compound was obtained(yield: 82%).

$^1$H NMR(CDCl₃) δ 0.83–0.99(m, 6H), 1.77(m, 1H), 2.61–3.24 (m, 8H), 3.74(m, 1H), 4.11(m, 1H), 4.95(m, 1H), 5.10(S, 2H), 7.21–7.50(m, 15H)

43-3) Preparation of [[(5S)-[(N-(2-quinolinecarbonyl)-L-asparaginyl]amino]-(4R,3S)-epoxy-6-phenyl-1-hexanoyl]-(2S)-[[1-phenyl-3-methyl]-butyl]amide(42)

To a solution of 263 mg(0.5 mmol) of the product obtained in Example 43-2) dissolved in 20 ml of methanol was added about 10% by weight of Pd/C and the reaction mixture was stirred under 1 atmosphere of hydrogen for 3 hours. The resulting solution was passed through celite to remove inorganic metal and the reaction solvent was removed. The resulting amine compound was added at 0° C. to a solution of 144 mg(0.5 mmol) of 2-quinolinecarboxylic acid and each 1.5 equivalent of EDC, HOBT and triethylamine in 10 ml of DMF. The resulting mixture was stirred at room temperature for 3 hours and then distilled under a reduced pressure to remove organic solvent. The residue was dissolved in 50 ml of ethyl acetate and washed with 50 ml of saturated NaHCO₃ solution. The organic layer was dried over anhydrous MgSO₄ and the residue was purified by column chromatography using 50% ethyl acetate/hexane as an eluent to give 197 mg of the title compound(yield: 62%).

$^1$H NMR(CDCl₃) δ 0.83–0.99(m, 6H), 1.76(m, 1H), 2.58–3.36 (m, 11H), 4.01–4.28(m, 2H), 5.01(d, 1H), 5.65(d, 1H), 6.29(m, 1H), 6.55(m, 1H), 6.94–8.35(m, 16H), 9.37(m, 1H)

FAB MS(M+1): 636

EXAMPLES 44 TO 51

The same procedures as described in Example 43 were repeated using corresponding starting material and reactants to obtain the compounds listed in Table 8.

TABLE 8

| Ex. No. (comp. No.) | compound | FABMS (M + 1) | $^1$H NMR δ |
|---|---|---|---|
| 44 (43) | (structure) | 622 | (CDCl$_3$) 0.85(d, 3H), 0.98(d, 3H), 1.88–2.31(m, 3H), 2.72–3.08(m, 5H), 3.32(s, 1H), 4.25(m, 1H), 4.75(m, 1H), 5.01(s, 1H), 5.52(bs, 1H) 6.20(bs, 1H), 6.99–8.36(m, 18H), 9.32(m, 1H) |
| 45 (44) | (structure) | 650 | (CDCl$_3$) 0.81–0.94(m, 6H), 1.64(m, 2H), 1.79(m, 1H), 2.58–3.19(m, 10H), 3.39(m, 1H), 3.85(m, 1H), 4.29(m, 1H), 5.01(m, 1H), 5.51(m, 1H), 6.02(d, 1H), 6.49(m, 1H), 6.99–8.36(m, 16H), 9.39(d, 1H) |
| 46 (45) | (structure) | 664 | (CDCl$_3$) 0.83–0.98(m, 6H), 1.25–1.57(m, 4H), 1.75(m, 1H), 2.58–3.39(m, 11H), 3.85(m, 1H), 4.25(m, 1H), 4.99(d, 1H), 5.62(d, 1H), 6.21–6.52(m, 2H), 6.99–8.34(m, 16H), 9.35(d, 1H) |
| 47 (46) | (structure) | 588 | (CDCl$_3$) 0.77–0.93(m, 12H), 1.78(m, 2H), 2.62–3.40(m, 9H), 3.65(m, 1H), 4.25(m, 1H), 4.99(m, 1H), 5.39–5.61(m, 2H), 6.01(m, 1H), 7.01–8.35(m, 11H), 9.35(d, 1H) |

TABLE 8-continued
| Ex. No. (comp. No.) | compound | FABMS (M + 1) | $^1$H NMR δ |
|---|---|---|---|
| 48 (47) | 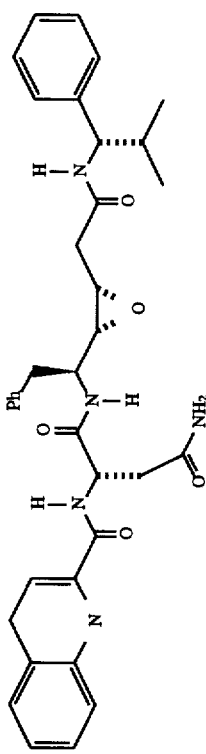 | 622 | (CDCl$_3$) 0.73(d, 3H), 0.95(d, 3H), 1.85–2.20(m, 3H), 2.70–3.02(m, 5H), 3.25(m, 1H), 4.02(m, 1H), 4.59(m, 1H), 4.95(m, 1H), 5.50(br, 1H), 5.91(br, 1H), 6.95–8.35(m, 18H), 9.29(m, 1H) |
| 49 (48) | 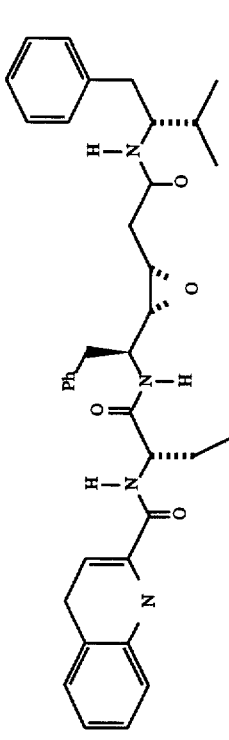 | 636 | (CDCl$_3$) 0.83–0.99(m, 6H), 1.76(m, 1H), 2.58–3.36(m, 11H), 4.01–4.28 (m, 2H), 5.01(d, 1H) 5.65(d, 1H), 6.29(m, 1H), 6.55(m, 1H), 6.94– 8.35(m, 16H), 9.37(m, 1H) |
| 50 (49) | 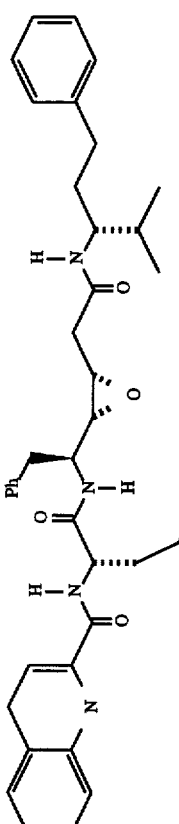 | 650 | (CDCl$_3$) 0.81–0.94(m, 6H), 1.64(m, 2H), 1.79(m, 1H), 2.58–3.19(m, 10H), 3.39(m, 1H), 3.85(s, 1H), 4.29(m, 1H), 5.01(m, 1H), 5.51(m, 1H), 6.02(d, 1H), 6.49(m, 1H), 6.99–8.36(m, 16H), 9.39(d, 1H) |
| 51 (50) | 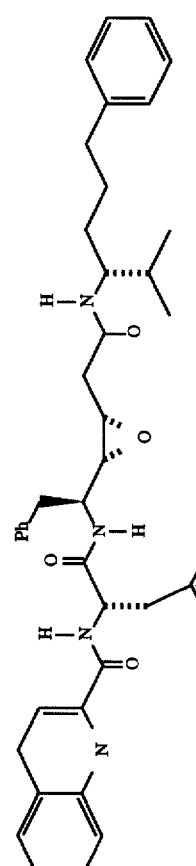 | 664 | (CDCl$_3$) 0.81–0.98(m, 6H), 1.25–1.60(m, 4H) 1.75(m, 1H), 2.53–3.39 (m, 11H), 3.85(m, 1H), 4.25(m, 1H), 4.99(d, 1H), 5.62(d, 1H), 6.21–6.52 (m, 2H), 6.99–8.34(m, 16H), 9.35(d, 1H) |

EXAMPLE 52

Preparation of 2-L-(t-butoxycarbonyl)amino-(3R, 4S)-epoxy-1,6-diphenylhexane(51)

To a stirred solution of 9.1 mg(0.026 mmol) of the compound obtained in Preparation Example 14-4) in 3 ml of dichloromethane was added 26.8 mg of metachloroperoxybenzoic acid (content:50%, 0.078 mmol) and the reaction mixture was refluxed for 6 hours. The reaction mixture was cooled to room temperature and diluted with 20 ml of dichloromethane. The resulting solution was washed successively with saturated $Na_2S_2O_3$ solution(10ml×2), saturated $NaHCO_3$ solution(10 ml×2) and distilled water(10 ml×2), dried over anhydrous $MgSO_4$ and distilled under a reduced pressure. The residue was purified by column chromatography using hexane:ethyl acetate (4:1) as an eluent to give 5.7 mg of the title compound(yield: 60%).

$^1$H NMR(CDCl$_3$) δ 1.39(11H, br), 2.40–3.05(6H, m), 3.70(1H, br), 4.80(1H, br), 7.02–7.34(10H, m)

EXAMPLE 53

Preparation of 2-L-(N-benzyloxycarbonyl-L-asparaginyl)amino-(3R, 4S)-epoxy-1,6-diphenylhexane (52)

The same procedures as described in Example 52 were repeated using the compound obtained in Preparation Example 15-2) except that the column chromatography was carried but using ethyl acetate:hexane(1:2) as an eluent to give the title compound(yield: 30%).

$^1$H NMR(CDCl$_3$) δ 1.5(2H, m), 2.4–3.0(8H, m), 3.9(1H, m), 4.4(1H, m), 5.1(2H, s), 5.4(1H, d), 5.6(1H, d), 6.4(2H, br), 7.0–7.4(15H, m)

Mass(FAB, m/e) 516(M+1)

EXAMPLE 54

Preparation of 2-L-(N-benzyloxycarbonyl-L-valinyl)amino-(3R,4S)-epoxy-1,6-diphenylhexane(53)

The same procedures as described in Example 53 were repeated using the compound obtained in Preparation Example 16 to give the title compound(yield: 65%).

$^1$H NMR(CDCl$_3$) δ 0.9(6H, m), 1.4(1H, m), 1.6(1H, m), 2.1(1H, m), 2.5–3.0(6H, m), 4.0(2H, m), 5.1(2H, s), 5.3 (1H, d), 6.1(1H, d), 7.1–7.4(15H, m)

Mass(FAB, m/e) 501(M+1)

EXAMPLE 55

Preparation of 2-L-(N-benzyloxycarbonyl-L-isoleucinyl)amino-(3R,4S)-epoxy-1,6-diphenylhexane (54)

The same procedures as described in Example 53 were repeated using the compound obtained in Preparation Example 17 to give the title compound(yield: 64%).

$^1$H NMR(CDCl$_3$) δ 0.9(6H, m), 1.0–1.7(4H, m), 1.9(1H, m), 2.5–3.1(6H, m), 4.0(2H, m), 5.1(2H, s), 5.3(1H, d), 6.1(1H, d), 7.1–7.4(15H, m)

Mass(FAB, m/e) 513(M+1)

EXAMPLE 56

Preparation of 2-L-(N-benzyloxycarbonyl-L-glutaminyl)amino-(3R,4S)-epoxy-1,6-diphenylhexane (55)

The same procedures as described in Example 53 were repeated using the compound obtained in Preparation Example 18 to give the title compound(yield: 49%).

$^1$H NMR(CDCl$_3$) δ 1.5(2H, m), 2.4–3.0(10H, m), 3.9(1H, m), 4.3(1H, m), 5.2(2H, s), 5.4(1H, d), 5.6(1H, d), 6.4(2H, br), 7.0–7.4(15H, m)

Mass(FAB, m/e) 530(M+1)

EXAMPLE 57

Preparation of 2-L-(N-phenoxyacetyl-L-asparaginyl) amino-(3R,4S)-epoxy-1,6-diphenylhexane(57)

25 mg of 2-L-(N-phenoxyacetyl-L-asparaginyl)amino-1, 6-diphenyl-hex-3-cis-ene was dissolved in 5 ml of dichloromethane. The same procedures as described in Example 53 were repeated using the above solution except that the column chromatography was carried out using ethyl acetate:hexane(1:1) as an eluent to give 3 mg of the title compound(yield: 20%).

$^1$H NMR(CDCl$_3$) δ 1.2–1.6(2H, m), 2.4–3.2(8H, m), 4.4(2H, s), 4.7(1H, m), 6.4(2H, br), 7.0–7.5(15H, m)

Mass(FAB, m/e) 516(M+1)

EXAMPLE 58

Preparation of 2-L-[N-(2,4-difluoro)phenoxyacetyl-L-asparaginyl]amino-(3R,4S)-epoxy-1,6-diphenylhexane(58)

25 mg of 2-L-[N-(2,4-difluoro)phenoxyacetyl-L-asparaginyl) amino-1,6-diphenyl-hex-3-cis-ene was dissolved in 5 ml of dichloromethane. The same procedures as described in Example 53 were repeated using the above solution except that column chromatography was carried out using ethyl acetate:hexane(1:1) as an eluent to give 5 mg of the title compound(yield: 30%).

$^1$H NMR(CDCl$_3$) δ 1.2–1.6(2H, m), 2.4–3.2(8H, m), 3.9(1H, m), 4.4(2H, s), 4.7(1H, m), 6.4(2H, br), 7.0–7.5 (13H, m)

Mass(FAB, m/e) 552(M+1)

EXAMPLE 59

Preparation of 2-L-(benzyloxycarbonyl)amino-3,4-epoxy-1,6-diphenylhexane

To a solution of 3.3 g(8.56 mmol) of the compound obtained in Preparation Example 19-3) in 50 ml of chloroform was added 2.94 g(content: 50%, 17.1 mmol) of metachloroperoxy-benzoic acid. The mixture was refluxed for 3 hours, cooled to room temperature, washed successively with 10% $Na_2S_2O_3$ solution(20 ml×2), saturated $NaHCO_3$ solution(20 ml×2) and distilled water(20 ml×2), and dried over anhydrous $MgSO_4$. The residue was purified by column chromatography using hexane:ethyl acetate(6:1) as an eluent to give 2.57 g of the title compound (yield: 75%).

$^1$H NMR(CDCl$_3$) δ 1.32–1.70(2H, m), 2.46–3.08(6H, m), 3.7(1H, m), 5.0(1H, d), 5.1(2H, s), 7.05–7.4(15H, m)

Mass(FAB, m/e) 402(M+1)

EXAMPLE 60

Preparation of 2-L-(N-benzyloxycarbonyl)-L-asparaginyl)amino-(3R,4S)-epoxy-1,6-diphenylhexane 60-1) Preparation of 2-amino-(3R,4S)-epoxy-1,6-diphenylhexane To a solution of 0.4 g(1 mmol) of the compound obtained in Example 59 in 10 ml of dry methanol was added 40 mg of 10% Pd/C and the mixture was stirred at room temperature under an atmosphere of hydrogen for 6 hours. The reaction mixture was filtered through celite and the filtrate was concentrated under a reduced pressure to give 0.26 g of the title compound (yield: 95%).

$^1$H NMR(CDCl$_3$) δ 1.3–1.6(2H, m), 2.35–3.0(7H, m), 7.0–7.3 (10H, m)

60-2) Preparation of 2-L-(N-benzyloxycarbonyl-L-asparaginyl) amino-(3R,4S)-epoxy-1,6-diphenylhexane 0.26 g(1 mmol) of the compound obtained in Example 60-1), 0.27 g(1 mmol) of N-benzyloxycarbonyl-L-asparagine, 0.29 g (1.5 mmol) of 3-ethyl-3'-(dimethylamino) propylcarbodiimide, 0.21 g(1.5 mmol) of N-hydroxybenzotriazol and 0.15 g(1.5 mmol) of triethylamine were dissolved in 8 ml of dry dimethylformamide and the reaction mixture was reacted with stirring at room temperature for 15 hours. After the reaction was completed, dimethylformamide was distilled off under a reduced pressure and the residue was dissolved in 50 ml of ethyl acetate. The solution was washed with 50 ml of saturated NaHCO$_3$ solution, and dried over anhydrous MgSO$_4$, and concentrated in vacuo. The residue was purified by column chromatography using ethyl acetate as an eluent to give 0.26 g of the title compound (yield: 50%). NMR and FABMS data of the title compound were the same as those of the compound obtained in Example 53.

EXAMPLE 61

Preparation of 2-L-[N-(N-benzyloxycarbonyl-L-alanyl)-L-asparaginyl]amino-(3R,4S)-epoxy-1,6-diphenylhexane(67)

The same procedures as described in Example 60-1) were used to remove benzyloxycarbonyl protecting group from the compound obtained in Example 60-2). The same procedures as described in Example 60-2) were repeated using the above resulting compound except that N-benzyloxycarbonyl-L-alanine was used in place of N-benzyloxycarbonyl-L-asparagine to give the title compound(yield: 50%).

$^1$H NMR(CD$_3$OD) δ 1.2–1.5(2H, m), 1.35(3H, d), 2.4–3.1 (8H, m), 3.9(1H, m), 4.1(1H, m), 4.7(1H, m), 5.12 (2H, s), 7.05–7.4(15H, m)

Mass(FAB, m/e) 587(M+1)

EXAMPLE 62

Preparation of 2-L-(N-2-quinolinecarbonyl-L-asparaginyl)amino-(3R,4S)-epoxy-1,6-diphenylhexane (62)

To a solution of 100 mg(0.2 mmol) of the compound obtained in Example 60-2) in 10 ml of dry methanol was added 10 mg of 10% Pd/C and the mixture was stirred at room temperature under an atmosphere of hydrogen for 6 hours. The resulting solution was filtered through Celite and methanol was removed by distillating under a reduced pressure. The residue was dissolved in 3 ml of dry dimethylformamide together with 41 mg(0.24 mmol) of 2-equinolinecarboxylic acid, 38 mg (0.2 mmol) of 3-ethyl-3'-(dimethylamino)propylcarbodiimide, 27 mg(0.2 mmol) of N-hydroxybenzotriazol and 24 mg(0.24 mmol) of triethylamine, and the reaction mixture was stirred at room temperature for 15 hours. After the reaction was completed, dimethylformamide was removed and the residue was dissolved in 40 ml of ethyl acetate. The solution was washed several times with water, dried over anhydrous MgSO$_4$ and distilled under a reduced pressure. The residue was purified by column chromatography using ethyl acetate:hexane (1:1) as an eluent to give 40 mg of the title compound(yield: 37%).

$^1$H NMR(CDCl$_3$) δ 1.4–1.7(2H, m), 2.3–3.0(8H, m), 4.1(1H, m), 5.0(1H, m), 5.5(1H, br), 6.0(1H, br), 6.7 (1H, s), 7.05–8.3(16H, m), 9.5(1H, dd)

Mass(FAB, m/e) 537(M+1)

EXAMPLE 63

Preparation of 2-L-(N-1-naphthoxyacetyl-L-asparaginyl)amino-(3R,4S)-epoxy-1,6-diphenylhexane (61)

The same procedures as described in Example 62 were repeated using 1-naphthoxyacetic acid in place of 2-quinolinecarboxylic acid to give the title compound(yield: 65%).

$^1$H NMR(CDCl$_3$) δ 1.4–1.7(2H, m), 2.3–3.0(8H, m), 4.0(1H, m), 4.6(2H, s), 4.9(1H, m), 5.6(1H, d), 6.1(1H, s), 6.8–7.8(1H, m), 8.4(1H, t), 8.6–8.7(1H, dd)

Mass(FAB, m/e) 566(M+1)

EXAMPLE 64

Preparation of 2-L-(N-quinoxaline-2-yl carbonyl-L-asparaginyl)amino-(3R,4S)-epoxy-1,6-diphenylhexane (63)

The same procedures as described in Example 60-1) were used to remove benzyloxycarbonyl protecting group from 150 mg (0.29 mmol) of the compound obtained in Example 60-2). The resulting compound was dissolved in 30 ml of dry dichloromethane together with 73 mg(0.38 mmol) of quinoxaline-2-yl carbonylchloride and 146 mg(1.45 mmol) of triethylamine and the reaction mixture was stirred under reflux for 10 hours. After the reaction was finished, the solution was washed twice with each 50 ml of saturated NaHCO$_3$ solution, dried over anhydrous MgSO$_4$ and distilled under a reduced pressure. The residue was purified by column chromatography using ethyl acetate as an eluent to give 54 mg of the title compound(yield: 34%).

$^1$H NMR(CDCl$_3$) δ 1.3–1.8(2H, m), 2.4–3.1(8H, m), 4.05(1H, m), 4.95(1H, m), 5.5(1H, br), 5.9(1H, d), 7.1–7.4 (10H, m), 7.5(1H, d), 7.9(1H, m), 8.2(1H, m), 9.2(1H, dd), 9.6(1H, s)

Mass(FAB, m/e) 538(M+1)

EXAMPLE 65

Preparation of 2-L-[N-(N-morpholinecarbonyl-L-alaninyl)-L-asparaginyl]amino-(3R,4S)-epoxy-1,6-diphenylhexane(60)

The compounds obtained in Example 60-2) and Preparation Example 20 were subjected to coupling reaction according to the procedures as described in Example 60-2) and the resulting residue was purified by column chromatography using ethyl acetate as an eluent to give of the title compound (yield: 58.4%).

$^1$H NMR(CDCl$_3$) δ 1.2–1.7(5H, m, d), 2.4–3.2(8H, m), 3.4(4H, br), 3.7(4H, br), 3.9(1H, m), 4.2(1H, m), 4.7 (1H, m), 5.3(1H, br), 5.7(1H, d), 6.2(1H, br), 7.0–7.5(10H, m), 7.8(1H, dd), 8.0(1H, d)

Mass(FAB, m/e) 565(M+1)

EXAMPLE 66

Preparation of 2-L-[N-(N-morpholinecarbonyl-L-phenylalaninyl)-L-asparaginyl]amino-(3R,4S)-epoxy-1,6-diphenylhexane(59)

The same procedures as described in Example 65 were repeated using the compound obtained according to the same procedures as described in Example 20 by using L-phenylalanine in place of L-alanine to give the title compound (yield: 54%).

$^1$H NMR(CDCl$_3$) δ 1.2–1.7(2H, m), 2.4–3.2(10H, m), 3.4(4H, br), 3.7(4H, br), 5.7(1H, d), 6.2(1H, br), 7.0–7.5 (15H, m), 7.6(1H, dd), 7.9(1H, d)

EXAMPLE 67

Preparation of 2-L-(N-3-triazolopropanecarbonyl-L-asparaginyl)amino-(3R,4S)-epoxy-1,6-diphenylhexane The same procedures as described in Example 60-1) were used to remove benzyloxycarbony protecting group from the compound obtained in Example 60-2). The same procedures as described in Example 60-2) were repeated using the above resulting compound except that 3-triazopropylic acid was used in place of N-benzyloxycarbonyl-L-asparagine to give the title compound(yield: 58%).

$^1$H NMR(CD$_3$OD) δ 1.2–1.6(2H, m), 2.4–3.2(10H, m), 3.9(1H, m), 4.5(2H, t), 4.75(1H, m), 7.0–7.4(10H, m), 8.0 (1H, s), 8.45(1H, s)

Mass(FAB, m/e) 505(M+1)

EXAMPLE 68

Preparation of 2-L-[N-(N-benzyloxycarbonyl-L-phenylalanyl)-L-asparaginyl]amino-(3R,4S)-epoxy-1,6-diphenylhexane(68)

The same procedures as described in Example 60-1) were used to remove benzyloxycarbony protecting group from the compound obtained in Example 60-2). The same procedures as described in Example 60-2) were repeated using the above resulting compound except that N-benzyloxycarbonyl-L-phenylalanine was used in place of N-benzyloxycarbonyl-L-asparagine to give the title compound(yield: 65%).

$^1$H NMR(CD$_3$OD) δ 1.2–1.5(2H, m), 2.4–3.1(10H, m), 3.9(1H, m), 4.3(1H, m), 4.7(1H, m), 5.05(2H, s), 7.0–7.5 (20H, m)

EXAMPLE 69

Preparation of 2-L-[N-(N-morpholinepropanecarbonyl-L-phenylalanyl)-L-asparaginyl]amino-(3R,4S)-epoxy-1,6-diphenylhexane(66)

The same procedures as described in Example 60-1) were used to remove benzyloxycarbony protecting group from the compound obtained in Example 68. The same procedures as described in Example 60-2) were repeated using the above resulting compound except that 3-morpholinepropionic acid was used in place of N-benzyloxycarbonyl-L-asparagine to give the title compound through recrystallization(yield: 63%).

Mass(FAB, m/e) 670(M+1)

EXAMPLE 70

Preparation of 2-L-[N-(N-oxy)quinoline-2-yl-carbonyl-L-asparaginyl]amino-(3R,4S)-epoxy-1,6-diphenylhexane(64)

70-1) Preparation of 2-L-(N-2-quinolinecarbonyl-L-asparaginyl) amino-(3R,4S)-epoxy-1,6-diphenylhexane The same procedures as described in Example 60-2) were repeated using the compound obtained in Example 60-1) except that N-(quinoline-2-yl-carbonyl)-L-asparagine was used in place of N-benzyloxycarbonyl-L-asparagine. The resulting residue was purified by column chromatography using ethyl acetate:hexane(1:2) as an eluent to give 60 mg of the title compound(yield: 40%).

$^1$H NMR(CDCl$_3$) δ 2.2–3.1(8H, m), 4.7(2H, m), 5.2(1H, t), 5.4(1H, m), 6.4(1H, d), 7.0–7.5(10H, m), 7.6–8.3(6H, m), 8.8(1H, dd)

70-2) Preparation of 2-L-[N-(N-oxy)quinoline-2-yl-carbonyl-L-asparaginyl]amino-(3R,4S)-epoxy-1,6-diphenylhexane 20 mg of the compound obtained in Example 70-1) was dissolved in 5 ml of dichloromethane and the same procedures as described in Example 59 were repeated using the above solution. The resulting residue was purified by column chromatography using ethyl acetate:hexane(1:1) as an eluent to give 45 mg of the title compound(yield: 25%).

$^1$H NMR(CDCl$_3$) δ 1.2–1.6(2H, m), 2.4–3.2(8H, m), 3.9(1H, m), 5.0(1H, m), 6.8(1H, d), 7.0–8.3(16H, m), 8.8 (1H, dd)

Mass(FAB, m/e) 553(M+1)

EXAMPLE 71

Preparation of 5-L-(N-benzyloxycarbonyl-L-asparaginyl)amino-(3S,4R)-epoxy-7-methyl-1-phenyloctane(56)

71-1) Preparation of 5-L-(N-benzyloxycarbonyl-L-asparaginyl) amino-7-methyl-1-phenyloct-3-cis-ene The same procedures as described in Example 60-2) were repeated using the compound obtained in Preparation Example 21-4) and the resulting residue was purified by column chromatography usng ethyl acetate:hexane(1:2) as an eluent to give 24 mg of the title compound(yield: 40%).

$^1$H NMR(CDCl$_3$) δ 0.9(6H, 2d), 1.1–1.56(3H, m), 2.3–3.0 (6H, m), 4.4(1H, m), 4.7(1H, m), 5.1(2H, s), 5.2(1H, m), 5.5(2H, m), 6.0(1H, d), 7.1–7.4(10H, m)

Mass(FAB, m/e) 466(M+1)

71-2) Preparation of 5-L-(N-benzyloxycarbonyl-L-asparaginyl) amino-(3S,4R)-epoxy-7-methyl-1-phenyloctane The same procedures as described in Example 59 were repeated using a solution of 10 mg of the compound obtained in Example 70-1) dissolved in 1 ml of dichloromethane and the resulting residue was purified by column chromatography using ethyl acetate:hexane(1:1) as an eluent to give 5 mg of the title compound(yield: 50%).

$^1$H NMR(CDCl$_3$) δ 0.9(6H, dd), 1.1–1.6(3H, m), 1.8(2H, m), 2.7–3.1(6H, m), 3.9(1H, m), 4.5(1H, m), 5.1 (2H, s), 5.6(1H, d), 6.3(1H, d), 7.1–7.4 (10H, m)

Mass(FAB, m/e) 482(M+1)

EXAMPLE 72

Preparation of 2-L-(benzyloxycarbonylamino)-(3R, 4S)-epoxy-7-methyl-1-phenyloctane The same procedures as described in Example 59 were repeated using a solution of 2.02 g of the compound obtained in Preparation Example 22 dissolved in 20 ml of chloroform and the resulting residue was purified by column chromatography using ethyl acetate:hexane(1:2) as an eluent to give total 0.8 g of product(yield: 50%), in which the title compound was 0.6 g(yield: 40%).

$^1$H NMR(CDCl$_3$) δ 0.8(6H, dd), 1.0–1.5(5H, m), 2.8–3.1 (4H, m), 3.8(1H, m), 5.05(2H, s), 7.1–7.4(10H, m)

EXAMPLE 73

Preparation of 2-L-(N-benzyloxycarbonyl-L-asparagyl)amino-(3R,4S)-epoxy-7-methyl-1-phenyloctane(69)

The same procedures as described in Example 60-1) were used to remove benzyloxycarbonyl protecting group from 500 mg (1.36 mmol) of the compound obtained in Example 72. The same procedures as described in Example 60-2) were repeated using the above resulting compound to give 400 mg of the title compound(yield: 55%).

$^1$H NMR(CD$_3$OD) δ 0.8(6H, d), 0.9–1.4(5H, m), 2.4–3.0 (6H, m), 3.8(1H, m), 4.4(1H, m), 5.0(2H, s), 7.0–7.4 (10H, m)

Mass(FAB, m/e) 483(M+1)

EXAMPLE 74

Preparation of 2-L-[N-(2-quinolinecarbonyl)-L-asparaginyl]amino-(3R,4S)-epoxy-7-methyl-1-phenyloctane(70)

150 mg(0.31 mmol) of the compound obtained in Example 72 was subjected to coupling reaction according to the same procedures as described in Example 62 and the resulting residue was purified by column chromatography using ethyl acetate as an eluent to give 60 mg of the title compound (yield: 40%).

$^1$H NMR(CDCl$_3$) δ 0.8(6H, dd), 0.9–1.6(5H, m), 2.6–3.0 (6H, m), 4.0(1H, m), 4.9(1H, m), 5.4(1H, br), 6.0 (1H, br), 7.0–7.3(5H, m), 7.4(1H, br), 7.6–8.3 (6H, m), 9.3(1H, dd)

Mass(FAB, m/e) 503(M+1)

EXAMPLE 75

Preparation of 2-L-[N-(N-morpholinesulfonyl-L-alaninyl)-L-asparaginyl]amino-(3R,4S)-epoxy-1,6-diphenylhexane(65)

The same procedures as descirbed in Example 60-1) were repeated to remove benzyloxycarbonyl protecting group from the compound obtained in Example 61 and the resulting compound was mixed with N-morpholinesulfonyl chloride. The resulting solution was stirred at room temperature for 4 hours and then distilled under a reduced pressure. The residue was purified by column chromatography using ethyl acetate as an eluent to give the title compound(yield: 70%).

Mass(FAB, m/e) 634(M+1)

EXAMPLE 76

Preparation of 4S-1,4-bis[N-(N'-benzyloxycarbonyl-L-valinyl)amino]-5-phenyl-(2S,3R)-(Z)-epoxypentane(71)

To a stirred solution of 115 mg(0.25 mmol) of 4S-1,4-bis[(N-benzyloxycarbonyl)amino]-5-phenyl-(2S,3R)-(Z)-epoxypentane obtained in Preparation Example 25 in 10 ml of dry methanol was added 20 mg of 10% Pd/C. The reaction mixture was stirred under an atmosphere of hydrogen for 3 hours to obtain 0.25 mmol of 1,4-(2S,3R,4S)-5-phenyl-2,3-(Z)-epoxypentanediamine(yield: 100%). The resulting solution was filtered through Celite to remove Pd/C and distilled under a reduced pressure to remove the organic solvent. The residue was dissolved in 5 ml of dry dimethylformamide together with 2.5 equivalent of N-benzyloxycarbonyl-L-valine, 3 equivalents of EDC, 3 equivalents of HOBT and 3 equivalents of triethylamine, and the mixture was stirred at room temperature for 16 hours. The resulting solution was distilled under a reduced pressure to remove the organic solvent. 30 ml of ethyl acetate was added to the residue and the resulting solution was washed with 50 ml of saturated NaHCO$_3$ solution. The organic layer was separated and dried over anhydrous MgSO$_4$ and concentrated in vacuo. The residue was purified by column chromatography using ethyl acetate as an eluent to give 124 mg of the title compound(yield: 75%).

$^1$H NMR(CDCl$_3$) 0.82–1.01(m, 12H), 2.10(m, 2H), 2.71–3.22(m, 6H), 3.62(m, 1H), 3.95(m, 1H), 4.11(m, 1H), 5.11 (d, 4H), 5.21(m, 1H), 5.60(d, 1H), 5.85(m, 1H), 6.20(d, 1H), 7.15–7.44(m, 15H)

FABMS 659(M+1)

EXAMPLE 77

Preparation of 4S-1,4-bis[N-(N'-benzyloxycarbonyl-L-glutamic acidyl)amino]-5-phenyl-(2S,3R)-(Z)-epoxypentane(74)

48 mg of diamine obtained in Example 76 and 2.1 equivalent of N-benzyloxycarbonyl-L-glutamic acid-γ-benzyl ester were subjected to the coupling reaction according to the same procedures as described in Example 76 and the resulting residue was purified by chromatography using ethyl acetate as an eluent to obtain the product. To a solution of the above product in 10 ml of dry methanol was added 20 mg of 10% Pd/C and the mixture was stirred under an atmosphere of hydrogen for 16 hours and then filtered through Celite to remove Pd/C. The filtrate was distilled under a reduced pressure to remove the organic solvent and the residue was dissolved in a mixture of water(20 ml) and dioxane(20 ml). 2.1 equivalent of benzyloxycarbonyl chloride and sodium bicarbonate solution was added slowly to the resulting solution and the mixture was stirred at room temperature for 4 hours. The resulting solution was distilled under a reduced pressure to remove dioxane, and the residue was washed with 30 ml of ether and adjusted to pH 3.5 with potassium hydrogensulfate. The resulting solution was extracted with ethyl acetate and the extract was purified by column chromatography using dichloromethane:methanol (3:1) as an eluent to give 93 mg of the title compound(yield: 52%).

$^1$H NMR(CD$_3$OD) 1.88(m, 2H), 2.15(m, 2H), 2.41–3.06 (m, 7H), 3.22(m, 1H), 3.40–3.59(m, 3H), 4.11(m, 1H), 4.44(m, 1H), 5.10(d, 4H), 7.10–7.39(m, 15H)

EXAMPLE 78

Preparation of 4S-1,4-bis[N-[(N'-benzylmethylamino)carbonyl-L-valinyl]amino]-5-phenyl-(2S,3R)-(Z)-epoxypentane(81)

48 mg of diamine compound obtained in Example 76 and 2 equivalents of N-[(N'-benzyl methyl amino)carbonyl]-L-valine-P-nitro phenyl ester were dissolved in 5 ml of dry dimethylformamide and the mixture was stirred at room temperature for 16 hours. The resulting solution was distilled under a reduced pressure to remove organic solvent and 30 ml of ethyl acetate was added to the residue. The resulting solution was washed with 50 ml of saturated NaHCO$_3$ solution and the organic layer was dried over anhydrous MgSO$_4$. The residue was purified by column chromatography over silica gel with dichloromethane:methanol(12:1) as an eluent to give 127 mg of the title compound(yield: 74%).

$^1$H NMR(CDCl$_3$) 0.72–0.98(m, 12H), 2.05(m, 2H), 2.80–3.03(m, 9H), 3.21(t, 1H), 3.61–3.74(m, 3H), 4.05–4.29 (m, 2H), 4.50(s, 4H), 4.55(d, 1H), 4.86(d, 1H), 6.99 (d, 1H), 7.11–7.35(m, 15H), 7.50–7.72(m, 1H)

FABMS 685(M+1)

EXAMPLE 79

Preparation of 4S-1,4-bis[N-(N'-benzyloxycarbonyl-L-valinyl)amino]-5-cyclohexyl-(2S,3R)-(Z)-epoxypentane(86)

To a solution of 117 mg(1.25 mmol) of 4S-1,4-bis[(N-benzyloxycarbonyl)amino]-5-cyclohexyl-(2S,3R)-(Z)- epoxypentane in 10 ml of dry methanol was added 20 mg of 10% Pd/C and the mixture was stirred for 3 hours under hydrogen condition (rubber balloon). The resulting solution was filtered through Celite to remove Pd/C and the filtrate was distilled under a reduced pressure to remove the organic solvent. The residue was dissolved in 5 ml of dry dimethyl formamide together with 2.5 equivalent of N-benzyloxycarbonyl-L-valine, 3 equivalents of EDC, 3 equivalents of HOBT and 3 equivalents of triethylamine. The resulting solution was stirred at room temperature for 16 hours and then distilled under a reduced pressure to remove the organic solvent. 30 ml of ethyl acetate was added to the residue and the solution was washed with 50 ml of saturated NaHCO$_3$ solution. The organic layer was dried over anhydrous MgSO$_4$ and the residue was purified by column chromatography using ethyl acetate as an eluent to give 123 mg of the title compound(yield: 74%).

$^1$H NMR(CDCl$_3$) 0.82–1.72(m, 25H), 2.03–2.29(m, 2H), 2.86(m, 2H), 3.31(m, 2H), 3.83–4.22(m, 3H), 5.10(s, 4H), 5.26(d, 1H), 5.86(d, 1H), 5.95(d, 1H), 6.72 (bs, 1H), 7.26–7.42(m, 10H)

FABMS 665(M+1)

EXAMPLE 80

Preparation of 4S-[N$^1$-[(N-benzyloxycarbonyl-L-asparaginyl)amino]]-[N$^4$-[(N-benzyloxycarbonyl-L-valinyl)amino]]-5-phenyl-(2S,3R)-(Z)-epoxypentane (76)

To a solution of 526 mg(0.8 mmol) of the product obtained in Preparation Example 27 in 20 ml of dry dichloromethane was added 3 equivalents of metachloroperoxybenzoic acid and the reaction mixture was stirred at room temperature for 16 hours. The organic layer was washed successively with 30 ml of 10% Na$_2$S$_2$O$_3$ solution and 30 ml of saturated NaHCO$_3$ solution, and dried over anhydrous MgSO$_4$. The residue was purified by column chromatography using dichloromethane:methanol(15:1) as an eluent to give 339 mg of the title compound(yield: 63%)

$^1$H NMR(CDCl$_3$) 0.82–1.01(m, 6H), 2.10(m, 1H), 2.71–2.97(m, 3H), 3.15–3.24(m, 3H), 3.62(m, 1H), 3.72(m, 1H), 4.01–4.10(m, 2H), 4.53(m, 1H), 5.09(d, 4H), 5.75(bs, 2H), 6.52–6.66(m, 2H), 7.12–7.43 (m, 15H), 7.83–8.01(m, 2H)

FABMS 674(M+1)

EXAMPLE 81

Preparation of 4S-[N$^1$-(t-butoxycarbonyl)amino]-[N$^4$-[(N-benzyloxycarbonyl-L-valinyl)amino]]-5-phenyl-(2S,3R)-(Z)-epoxypentane(82)

To a solution of 298 mg(0.7 mmol) of the product obtained in Preparation Example 29 in 20 ml of dry methanol was added 40 mg of 10% Pd/C and the mixture was stirred under an atmosphere of hydrogen for 2 hours. The reaction mixture was filtered through Celite to remove Pd/C. The filtrate was concentrated to dryness and the residue was dissolved in 10 ml of dimethyl-formamide together with 1.2 equivalent of N-benzyloxycarbonyl-L-valine, 1.5 equivalent of EDC, 1.5 equivalent of HOBT and 1.5 equivalent of triethylamine and the mixture was stirred at room temperature for 16 hours. The resulting solution was distilled under a reduced pressure to remove the organic solvent and 50 ml of ethyl acetate was added to the residue. The resulting solution was washed with saturated NaHCO$_3$ solution and the organic layer was dried over anhydrous MgSO$_4$. The concentrated residue was purified by column chromatography using ethyl acetate as an eluent to give 250 mg of the title compound(yield: 68%).

$^1$H NMR(CDCl$_3$) 0.82–1.01(m, 6H), 1.41(s, 9H), 2.12(m, 1H), 2.75–3.14(m, 4H), 3.84–4.37(m, 4H), 5.11(s, 2H), 5.27(d, 1H), 6.12(d, 1H), 6.27(d, 1H), 7.20–7.43 (m, 10H)

FABMS 526(M+1)

EXAMPLES 82 TO 97

The same procedures as described in any of Example 76 to Example 81 were repeated using the corresponding intermediate respectively to obtain the compounds listed in Table 9 below. NMR and FABMS data are also shown in Table 9. (N-benzyloxycarbonyl)-L-cyclohexyl phenylalanal was prepared according to a method described by Boger et al. in J. Med. Chem. 28, 1779(1985).

TABLE 9

| Ex. No. (comp. No.) | compound | FABMS (M + 1) | ¹H NMR |
|---|---|---|---|
| 82 (72) | | 689 | (DMSO) 2.30–2.49(m, 2H), 2.62–3.09(m, 2H), 3.18(d, 4H), 3.72(m, 1H), 4.11(m, 2H), 4.32(m, 2H), 5.05(d, 4H), 6.18–6.24(m, 2H), 6.86(bs, 2H), 7.10–7.45(m, 15H), 8.02–8.23(m, 2H) |
| 83 (73) | | 663 | (CDCl₃) 1.01–1.29(m, 6H), 2.70–3.28(m, 4H), 3.50(m, 2H), 3.81(m, 1H), 3.95–4.66(m, 4H), 5.10(s, 4H), 5.75–6.31(m, 4H), 7.12–7.41(m, 15H) |
| 84 (75) | | 674 | (CDCl₃) 0.82–1.02(m, 6H), 2.12(m, 2H), 2.68–3.12(m, 4H), 3.20(d, 2H), 3.57(m, 1H), 3.72(m, 1H), 3.95–4.03(m, 2H), 4.52(m, 1H), 5.10(d, 4H), 5.19(d, 1H), 5.75(bs, 2H), 6.59(bs, 2H), 7.09–7.42(m, 15H), 7.89(m, 1H) |
| 85 (77) | | 661 | (CDCl₃) 0.72–1.01(m, 12H), 2.05(m, 2H), 2.81–3.19(m, 4H), 3.65(m, 1H), 3.82–4.49(m, 4H), 5.19(s, 4H), 5.41(d, 1H), 5.60(d, 1H), 5.80(d, 1H), 6.71(d, 1H), 7.09–7.38(m, 9H), 7.67(t, 2H), 8.53(bs, 2H) |
| 86 (78) | | 661 | (CDCl₃) 0.71–1.02(m, 12H), 1.91(m, 1H), 2.07(m, 1H), 2.70–3.22 (m, 4H), 3.60(m, 1H), 3.91(m, 1H), 4.05–4.22(m, 2H), 4.49(m, 1H), 5.09(s, 4H), 5.50(m, 1H), 5.69(bs, 1H), 6.02(m, 1H), 6.72(bs, 1H), 7.12–7.33(m, 7H), 7.67(d, 2H), 8.58(d, 4H) |

TABLE 9-continued
| Ex. No. (comp. No.) | compound | FABMS (M + 1) | 1H NMR |
|---|---|---|---|
| 87 (79) | 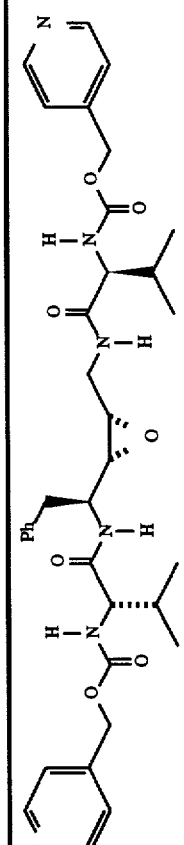 | 661 | (CDCl$_3$) 0.72–1.01(m, 12H), 2.07(m, 2H), 2.75–3.26(m, 4H), 3.59(m, 1H), 3.95(m, 1H), 4.03–4.21(m, 2H), 4.46(m, 1H), 5.11(s, 4H) 5.67(d, 1H), 5.99 (m, 1H), 6.67(bs, 1H), 7.12–7.33(m, 9H), 7.62–7.89(m, 1H), 8.52(s, 4H) |
| 88 (80) | 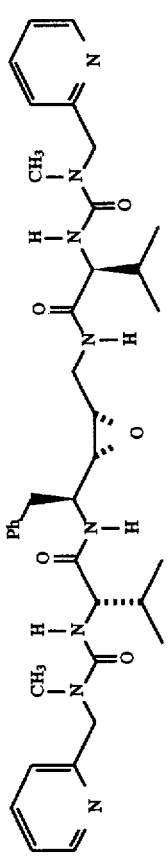 | 687 | (CDCl$_3$) 0.83–1.02(m, 12H), 2.18(m, 2H), 2.72–3.08(m, 9H), 3.23(m, 1H), 3.61(m, 1H), 3.91–4.15(m, 2H), 4.38–4.62(m, 6H), 6.16(s, 1H), 6.35(m, 1H), 6.55(d, 1H), 6.75(bs, 1H), 7.09–7.32(m, 9H), 7.69(m, 2H), 8.52(bs, 2H) |
| 89 (83) | 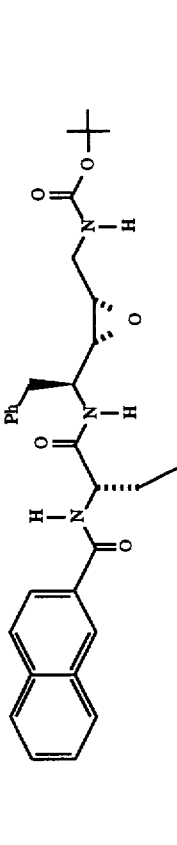 | 562 | (CDCl$_3$) 1.41(s, 9H), 2.64–3.22(m, 6H), 3.82(m, 1H), 4.05(m, 2H), 4.51(m, 1H), 5.11 5.85(d, 1H), 6.42(bs, 2H), 6.95(bs, 1H), 7.09–8.32(m, 10H), 9.41(d, 1H) |
| 90 (84) | 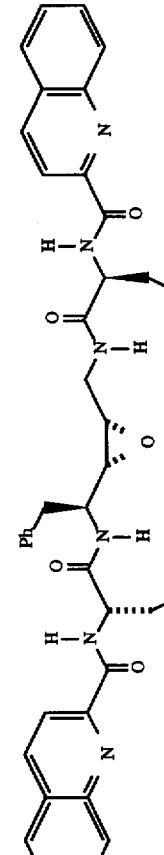 | 731 | (DMSO) 2.42–3.09(m, 4H), 3.16(bs, 4H), 3.65–4.02(m, 3H), 4.45(m, 1H), 4.71(m, 1H), 5.60(bs, 1H), 5.85(bs, 2H), 6.92(bs, 3H), 7.09–8.26(m, 17H), 8.58(d, 1H), 8.99.19(m, 1H) |

TABLE 9-continued

| Ex. No. (comp. No.) | compound | FABMS (M + 1) | ¹H NMR |
|---|---|---|---|
| 91 (85) | | 695 | (DMSO) 0.74–1.75(m, 13H), 2.91–3.05(m, 2H), 3.19(d, 4H), 3.95(m, 1H), 4.26–4.45(m, 4H), 5.02(s, 4H), 5.25(m, 1H), 5.85(bs, 2H), 6.72(bs, 2H), 6.97(bs, 2H) 7.10–7.42(m, 10H), 8.02(bs, 1H) |
| 92 (87) | | 899 | (CDCl$_3$) 1.89(m, 2H), 2.11(m, 2H), 2.35(m, 4H), 2.72–2.97(m, 3H), 3.19(m, 1H), 3.45–3.53(m, 3H), 4.15(m, 1H), 4.49(m, 1H), 5.05(bs, 8H), 5.75–5.99(m, 3H), 6.99(d, 1H), 7.05–7.33(m, 25H) |
| 93 (88) | | 589 | (CDCl$_3$) 0.82–0.99(m, 6H), 2.08(1H), 2.70–3.29(m, 8H), 4.10(m, 1H), 4.38 (m, 1H), 5.01(m, 1H), 6.18(bs, 1H), 7.05–8.41(m, 16H), 9.27(m, 1H) |
| 94 (89) | | 547 | (CDCl$_3$) 2.69–3.31(m, 10H), 3.89(m, 1H), 4.12(m, 1H), 5.01(m, 1H), 6.11(bs, 2H), 7.05–8.36(m, 15H), 9.30(m, 1H) |

TABLE 9-continued

| Ex. No. (comp. No.) | compound | FABMS (M + 1) | ¹H NMR |
|---|---|---|---|
| 95 (90) | (structure) | 603 | (DMSO) 0.70–0.85(m, 6H), 1.01(m, 1H) 1.36(m, 1H), 1.69(m, 1H), 2.58–3.23(m, 8H), 3.81(m, 1H), 4.20(t, 1H), 4.81 (m, 1H), 6.91(bs, 2H), 7.05–9.03(m, 16H) |
| 96 (91) | (structure) | 623 | (DMSO) 2.66–3.31(m, 8H), 3.86(m, 1H) 4.85(m, 1H), 5.50(m, 1H), 6.95(bs, 1H) 7.05–9.09(m, 21H) |
| 97 (92) | (structure) | 637 | (DMSO) 2.65–3.25(m, 10H), 3.79(m, 1H), 4.52(m, 1H), 4.81(m, 1H), 6.91(s, 1H), 7.04–9.03(m, 22H) |

Assay for inhibitory effect on HIV protease

The inhibitory effect on HIV protease of the compounds of the present invention was determined by the following method.

To a buffer solution comprising 50 mM sodium acetate, pH 5.5, 1 mM dithiothreitol(DTT), 1 mM ethylenediaminetetraacetate (EDTA), 0.75M ammonium sulfate, 0.2M sodium chloride and 0.1% NP40(NONIDET P-40; Sigma Chemical Co., U.S.A.), were added various concentrations of a compound selected from Compound Nos. 1 to 92 to prepare a preincubation solution. Inhibition reaction was started with the addition of 2.6 nM of HIV-1 protease to the preincubation solution. Each 10 μl of the reaction solution was taken at a given time interval and added to 80 μl of assay solution containing 100 μM of reaction substrate in the same buffer solution as above to assay for the residual enzyme activity. In this context, an oligopeptide($K_M$=20 μM) consisting of 11 amino acids, i.e., Ser-Ile-Ala-Glu-(p-$NO_2$)-Phe-Leu-Val-Arg-Ala-Lys-His, was used as a reaction substrate, which oligopeptide was to be cleaved in two by the breakage of amide bond between (P-$NO_2$)-Phe and Leu upon the attack of HIV protease. The reaction rate was determined by subjecting the substrate before the reaction and the product after the reaction to HPLC separation and then measuring the relative amount of the product, using the strong absorbance of (p-$NO_2$)-Phe at 280 nm. The amount of reduction in enzyme activity according to the elasped time were measured and the natural logarithmic values(ln) of the measured amounts were plotted against time to obtain a linear graph and $k_{obs}$ was calculated from the slope of the linear graph.

The inhibition constant was calculated according to the following equation:

$$\frac{1}{k_{obs}} = \frac{1}{k_{ina}} + \frac{K_I}{k_{ina}} \cdot \frac{1}{[I]}$$

wherein:

$k_{obs}$ is a rate constant indicating the rate of reduction in enzyme activity according to the elapsed time under the presence of a given concentration of inhibitor, $k_{ina}$ is a rate constant indicating the rate of chemical reaction forming covalent bond between an enzyme and an inhibitor in Michaelis-Menten complex, $K_I$ is an inhibition constant indicating the dissociation rate of Michaelis-Menten complex into an enzyme and an inhibitor, and

[I] means the inhibitor concentration.

The above equation is applicable to an experiment carried out under the condition in which the concentration of inhibitor is far higher than that of enzyme(Steady State Kinetic). In case that the experiment was carried out under the condition in which the concentrations of inhibitor and enzyme were about the same, because of the superior inhibition effect of the inhibitor, the mechanism equation of

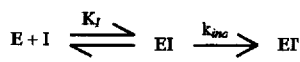

(wherein, E means an enzyme, I means an inhibitor, EI means a Michaelis-Menten complex and EI' means a complex having convalent bond formed between an enzyme and an inhibitor); and $K_I$ and $k_{ina}$ have the same meanings as defined above) was used to calculate the relative concentration of active enzyme, i.e., [E]/([E]+[EI]+[EI']) in every given time. The inhibition constants $K_I$ and $k_{ina}$ and second order rate constant $k_{ina}/K_I$ were obtained by inputting the value of [E]/([E]+[EI]+[EI']) into KINSIM/FITSIM program. FIG. 1 exemplifies a result of the experiment determining the binding ratio of enzymes and inhibitors, which result was obtained by reacting the enzyme and the inhibitor in various concentration ratios for a sufficient time period(at least for 30 minutes), and then plotting the relative activity of the remaining enzyme against [conc. of inhibitor]/[conc. of enzyme].

FIG. 1 was obtained using Compound No. 27; however, other compounds of the present invention are believed to yield substantially same results. The stoichiometric ratio of inhibitor to enzyme was 1:1; and this proves that one inhibitor is required to inactivate one enzyme. The above result gives a basis for inputting the said mechanism equations into KINSIM/FITSIM program.

The activity of HIV protease inactivated by any inhibitor of the present invention failed to return or recover even after a vigorous dialysis for 24 hours. The inhibition constants obtained in the above assay are shown in Table 10 below; and the results fully demonstrate that the compounds of the present invention inhibits HIV protease irreversibly.

TABLE 10

| Compound No. | $K_I$(μM) | $k_{ina}$(min$^{-1}$) | $k_{ina}/K_I$ (min$^{-1}$M$^{-1}$) |
|---|---|---|---|
| 2 | 0.018 | 0.22 | 1.2 × 10$^7$ |
| 3 | 0.040 | 0.12 | 3.0 × 10$^6$ |
| 4 | 0.060 | 0.09 | 1.5 × 10$^6$ |
| 5 | 0.092 | 0.20 | 2.2 × 10$^6$ |
| 6 | 0.42 | 0.13 | 3.1 × 10$^5$ |
| 7 | 0.33 | 0.10 | 3.0 × 10$^5$ |
| 8 | 0.060 | 0.12 | 2.0 × 10$^6$ |
| 9 | 0.055 | 0.11 | 2.0 × 10$^6$ |
| 10 | 1.057 | 0.15 | 1.4 × 10$^5$ |
| 11 | 0.11 | 0.20 | 1.8 × 10$^6$ |
| 12 | 0.37 | 0.30 | 8.1 × 10$^5$ |
| 13 | 0.52 | 0.43 | 8.3 × 10$^5$ |
| 14 | 0.35 | 0.25 | 7.1 × 10$^5$ |
| 15 | 0.92 | 0.22 | 2.4 × 10$^5$ |
| 16 | 0.42 | 0.15 | 3.6 × 10$^5$ |
| 19 | 0.081 | 0.22 | 2.7 × 10$^6$ |
| 22 | 0.042 | 0.09 | 2.1 × 10$^6$ |
| 25 | 0.020 | 0.18 | 9.0 × 10$^6$ |
| 26 | >10 | — | — |
| 27 | 0.003 | 0.20 | 6.7 × 10$^7$ |
| 28 | 0.015 | 0.20 | 1.3 × 10$^7$ |
| 29 | >10 | — | — |
| 30 | 0.022 | 0.20 | 1.1 × 10$^7$ |
| 32 | 0.005 | 0.22 | 4.4 × 10$^7$ |
| 34 | 0.015 | 0.16 | 1.1 × 10$^7$ |
| 35 | >10 | — | — |
| 38 | >10 | — | — |
| 39 | >10 | — | — |
| 40 | 0.033 | 0.25 | 7.6 × 10$^6$ |
| 41 | 0.045 | 0.19 | 4.2 × 10$^6$ |
| 42 | 0.008 | 2.6 | 3.3 × 10$^9$ |
| 43 | 0.0032 | 1.7 | 5.3 × 10$^8$ |
| 44 | 0.011 | 2.5 | 2.3 × 10$^8$ |
| 45 | 0.0012 | 2.4 | 2.0 × 10$^9$ |
| 46 | 0.0009 | 0.16 | 1.8 × 10$^8$ |
| 47 | 0.012 | 2.3 | 1.9 × 10$^8$ |
| 48 | 0.6 | 2.1 | 3.5 × 10$^6$ |
| 49 | 0.8 | 1.8 | 2.3 × 10$^6$ |
| 50 | 0.95 | 1.5 | 1.6 × 10$^6$ |
| 51 | 7.0 | 0.05 | 7.1 × 10$^3$ |
| 52 | 0.10 | 0.03 | 3.0 × 10$^5$ |
| 53 | 0.091 | 0.09 | 9.9 × 10$^5$ |
| 54 | 1.0 | 0.45 | 4.5 × 10$^5$ |
| 55 | 2.2 | 0.22 | 1.0 × 10$^5$ |
| 56 | 44.4 | 0.29 | 6.5 × 10$^3$ |
| 57 | 12.5 | 0.09 | 7.2 × 10$^3$ |
| 58 | 3.3 | 0.03 | 9.1 × 10$^3$ |

TABLE 10-continued

| Compound No. | $K_I(\mu M)$ | $k_{ina}(min^{-1})$ | $k_{ina}/K_I$ $(min^{-1}M^{-1})$ |
|---|---|---|---|
| 61 | 0.25 | 0.03 | $1.2 \times 10^5$ |
| 62 | 0.13 | 0.11 | $8.5 \times 10^5$ |
| 63 | 0.25 | 0.29 | $1.2 \times 10^6$ |
| 64 | 3.6 | 0.09 | $2.5 \times 10^4$ |
| 66 | 0.55 | 0.77 | $1.4 \times 10^6$ |
| 67 | 0.26 | 0.07 | $2.7 \times 10^5$ |
| 68 | 4.0 | 0.04 | $1.0 \times 10^4$ |
| 69 | 0.55 | 0.06 | $1.1 \times 10^5$ |
| 70 | 0.31 | 0.12 | $3.9 \times 10^5$ |
| 71 | 0.00018 | 0.14 | $7.7 \times 10^7$ |
| 72 | 0.11 | 0.22 | $2.0 \times 10^6$ |
| 73 | >10 | — | — |
| 74 | >10 | — | — |
| 75 | >10 | — | — |
| 76 | 2.0 | 0.046 | $2.3 \times 10^4$ |
| 77 | 0.1 | 0.24 | $2.4 \times 10^6$ |
| 78 | 0.72 | 0.10 | $1.4 \times 10^5$ |
| 79 | 3.0 | 0.10 | $3.3 \times 10^4$ |
| 80 | 0.15 | 0.32 | $2.1 \times 10^6$ |
| 81 | >10 | — | — |
| 82 | 0.45 | 1.1 | $2.4 \times 10^6$ |
| 83 | 0.40 | 1.2 | $3.0 \times 10^6$ |
| 84 | 0.50 | 0.2 | $4.0 \times 10^5$ |
| 85 | >10 | — | — |
| 86 | 0.05 | 0.2 | $4.0 \times 10^6$ |
| 88 | 0.85 | 2.2 | $2.6 \times 10^6$ |
| 90 | 0.14 | 0.4 | $2.9 \times 10^6$ |
| 91 | 1.20 | 0.3 | $2.5 \times 10^5$ |
| 92 | 1.4 | 0.2 | $1.4 \times 10^5$ |

Determination of anti-viral activity and cytotoxicity

The anti-viral activity of the compounds of the present invention was determined by measuring the concentration of the compounds that inhibits the proliferation of HIV by 50%($IC_{50}$) through a survey for syncytium formation or reverse transcriptase assay. $1 \times 10^5$ cells of each of H9(ATCC HTB 176) and Sup T1 cell lines were added to the wells of a 24-well microtiter plate and various concentrations of the compounds of the present invention were added thereto. 200 $TCID_{50}$(200-fold of 50% tissue culture infection dose) of HIV-1 inoculum and rpmi-1640 medium(Sigma Chemical Co., U.S.A) were added successively to the wells and the plate was incubated at 37° C. In case of Sup T1, the number of syncytium formed was investigated after 3 to 9 days. $IC_{50}$ of each compound was determined by measuring the concentration of inhibitor that can reduce the number of syncytium by 50% compared with those formed in the same condition without the inhibitor.

In case of H9, three-quarters(¾) of the culture medium in volume was refreshed every 3 days; and 6 ml of the culture fluid was centrifuged at 1000 rpm for 10 minutes. To 5 ml of the resulting supernatant were added 2.5 ml of 30% polyethyleneglycol(PEG, M.W. 6000-8000) and 0.4M NaCl. The resulting solution was allowed to stand at 0° C. overnight to precipitate virus particles. The solution was centrifuged at 2000 rpm for 45 minutes, the supernatant was discarded therefrom and the precipitate was diluted with 20 μl of a reverse transcriptase suspension buffer(50 mM tris-HCl, pH 7.5, 1 mM dithiothreitol, 20% glycerol, 0.25M KCl and 0.25% Triton X-100). The resulting suspension was stored in an Effendorf tube at −70° C. until used. A procedure of freezing said virus suspension for 2 minutes in dry ice and thawing same at 37° C. for 2 minutes was repeated three times and the resulting suspension was centrifuged at 4° C. The resulting supernatant was used in carrying out the reverse transcriptase assay.

10 μl of the said viral suspension was added to a solution of: 10 μl of buffer solution(250 mM tris-HCl, pH 7.5, 37.5 mM $MgCl_2$, 0.25% triton X-100), 1.2 μl of 200 mM dithiothreitol, 5 μl of 10 μM oligo(dT)-poly(A)(Boeringer Manheim, 12-18 oligomer), 1 μl(1 μCi) of $^3$H-TTP (Thymidinetri-phosphate) and 23.6 μl of water; and the resulting mixture was placed at 37° C. After 1 hour, the mixture was poured onto a WHATMAN DEB1 filter and the filter was washed three times with 5 ml of 2×SSC buffer solution(17.53 g of sodium chloride, 8.82 g of sodium citrate, pH 7.0, 1 liter of water) for about 10 minutes each time and twice with 95% ethanol for 10 seconds. The filter was put onto aluminium foil and dried with an infra-red lamp. The amount of radioactivity was counted using a liquid scintillation counter. $IC_{50}$ of each compound was determined by measuring the concentration of inhibitor that can reduce the activity of reverse transcriptase by 50%.

To determine the cytotoxicity of the compounds of the present invention, 0.1 μM to 100 μM of the novel compounds were added to H9 cell or Sup T1 cell and the mixture was cultured on a rpmi-1640 medium at 37° C. The medium was refreshed every 3 days and the extent of cell proliferation was observed using Hemacytometer according to the trypan blue dye exclusion technique which is well known in the art. $CT_{50}$(i.e., concentration that causes death of cells by 50%) was determined. For reference, AZT(Burrows-Wellcome), A-75925 (Abbott, $C_2$ symmetric compound) and Ro-31-8959(F. Hofmann-La Roche) were used as control compounds. Table 11 shows the anti-viral activities($IC_{50}$) and cytotoxicities($CT_{50}$) of the tested compounds of the present invention and the above control compounds.

TABLE 11

| Example No. | $IC_{50}(\mu M)$ | $CT_{50}(\mu M)$ |
|---|---|---|
| 2 | 0.2 | >100 |
| 3 | 3.0 | >100 |
| 6 | 5.0 | >100 |
| 7 | 4.0 | >100 |
| 8 | 7.0 | >100 |
| 9 | 8.0 | >100 |
| 12 | 7.0 | >100 |
| 13 | 10.0 | >100 |
| 14 | 9.0 | >100 |
| 19 | 5.0 | >100 |
| 22 | 4.0 | >100 |
| 25 | 0.5 | >100 |
| 26 | 0.5 | >100 |
| 27 | 1.0 | ~10 |
| 28 | 0.6 | >100 |
| 32 | 0.5 | >100 |
| 35 | 1.0 | >100 |
| 39 | 1.0 | >100 |
| 40 | 0.7 | >100 |
| 41 | 1.0 | >100 |
| 42 | 0.02 | >100 |
| 43 | 0.05 | >100 |
| 44 | 0.3 | >100 |
| 45 | 0.2 | >100 |
| 46 | 0.04 | >100 |
| 47 | 0.07 | >100 |
| 48 | 0.5 | ~5 |
| 49 | >5 | >100 |
| 50 | >5 | >100 |
| 52 | 0.7 ~ 1.2 | >100 |
| 53 | 1.0 ~ 1.5 | >100 |
| 61 | 1.0 ~ 2.0 | >100 |
| 62 | 0.2 ~ 0.7 | >100 |
| 63 | 1.0 ~ 2.0 | >100 |
| 70 | 5.0 | >100 |
| 71 | 0.08 | >100 |
| 72 | 0.5 | >100 |

TABLE 11-continued

| Example No. | $IC_{50}(\mu M)$ | $CT_{50}(\mu M)$ |
|---|---|---|
| 73 | 5 | >100 |
| 75 | 1 | >10 |
| 76 | 1 | >100 |
| 77 | 1 | >100 |
| 80 | 0.5 | >100 |
| 82 | 0.75 | >10 |
| 83 | 0.75 | >10 |
| 84 | 1 | >100 |
| 85 | 5 | >100 |
| 86 | 0.5 | >100 |
| AZT | 0.1 | >100 |
| A-75925 | 0.25 | >100 |
| Ro-31-8959 | 0.04 | >100 |

As can be seen from the above results, the compounds of the present invention are superior HIV protease inhibitors having a higher inhibition effect and lower cytotoxicity than those of the prior art.

While the present invention has been shown and described with reference to the particular embodiments, it will be apparent to those skilled in the art that many changes and modifications may be made without departing from the spirit and scope of the invention as defined in the appended claims.

What is claimed is:

1. Cis-epoxide compounds of formula (I-3) and pharmaceutically acceptable salts, hydrates and solvates thereof:

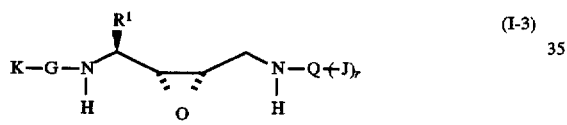

(I-3)

wherein:

$R^1$ is a cycloalkyl, or aryl-substituted lower alkyl group;

K and J are independently a group having the formula of

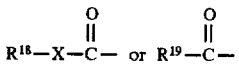

wherein $R^{18}$ is a lower alkyl group optionally substituted with an aryl radical; X is O, NH, or N—$CH_3$; and $R^{19}$ is an aromatic heterocyclic system containing a nitrogen atom in its ring, or a lower alkyl group optionally substituted with an aryl radical, or a hydrogen;

G is an amino acid which is linked to K— and

by peptide bonds in formula (I-3);

Q is an amino acid which is linked to

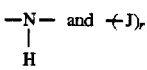

by peptide bonds in formula (I-3), or a group having the formula of

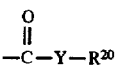

wherein $R^{20}$ is a lower alkyl group optionally substituted with an aromatic radical; and Y is $CH_2$, O or NH; and r is 0 or 1, except that Q is a group having the formula of

r is 0.

* * * * *